(12) United States Patent
Lee et al.

(10) Patent No.: US 8,507,255 B2
(45) Date of Patent: *Aug. 13, 2013

(54) COATING SYSTEM COMPRISING SYNZYME FOR DEGRADATION OF THREAT AGENTS

(75) Inventors: Yongwoo Lee, Waltham, MA (US);
Tomasz Modzelewski, Lawrenceville, NJ (US); John P. Puglia, Townsend, MA (US); Steven E. Weiss, Auburndale, MA (US); Robert A. Reinstein, Malden, MA (US)

(73) Assignee: Foster-Miller, Inc., Waltham, MA (US)

( * ) Notice: Subject to any disclaimer, the term of this patent is extended or adjusted under 35 U.S.C. 154(b) by 434 days.

This patent is subject to a terminal disclaimer.

(21) Appl. No.: 12/802,956

(22) Filed: Jun. 17, 2010

(65) Prior Publication Data

US 2011/0124079 A1    May 26, 2011

Related U.S. Application Data

(60) Provisional application No. 61/281,900, filed on Nov. 24, 2009.

(51) Int. Cl.
*A62D 3/00* (2007.01)
*C12N 11/08* (2006.01)
*C12N 11/06* (2006.01)

(52) U.S. Cl.
USPC .................. 435/262.5; 435/180; 435/181

(58) Field of Classification Search
None
See application file for complete search history.

(56) References Cited

U.S. PATENT DOCUMENTS

| | | | | |
|---|---|---|---|---|
| 4,421,850 A | * | 12/1983 | Daniels et al. | 435/41 |
| 5,521,101 A | * | 5/1996 | Saini et al. | 205/777.5 |
| 6,831,173 B1 | * | 12/2004 | Jetten et al. | 536/123.1 |
| 7,067,294 B2 | * | 6/2006 | Singh et al. | 435/174 |
| 7,192,766 B2 | * | 3/2007 | Shah et al. | 435/287.1 |
| 7,270,973 B2 | * | 9/2007 | Singh et al. | 435/18 |

* cited by examiner

*Primary Examiner* — David M Naff
(74) *Attorney, Agent, or Firm* — Iandiorio Teska & Coleman, LLP

(57) ABSTRACT

Sorption reinforced catalytic coating system for the degradation of threat agents including a synzyme coating about a material configured for the degradation of the threat agents, the synzyme coating including bucket-shaped molecules configured for the sorption of the threat agents A binding agent is configured for synzyme immobilization to maximize loading and retention of the synzyme coating on the material.

30 Claims, 24 Drawing Sheets

Calixarene

FIG. 15

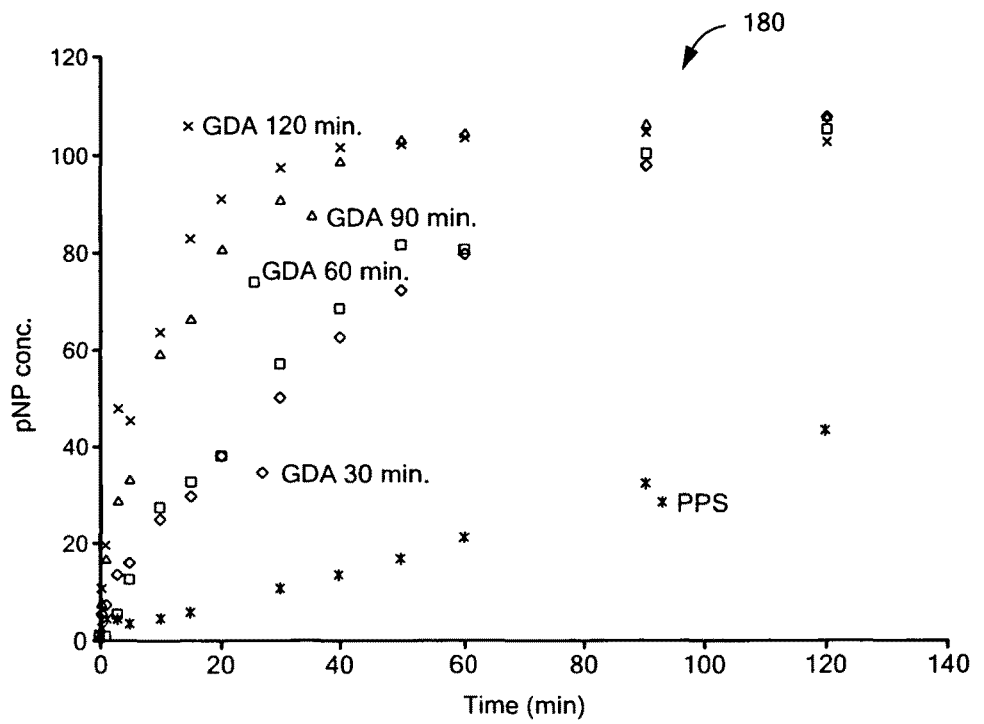
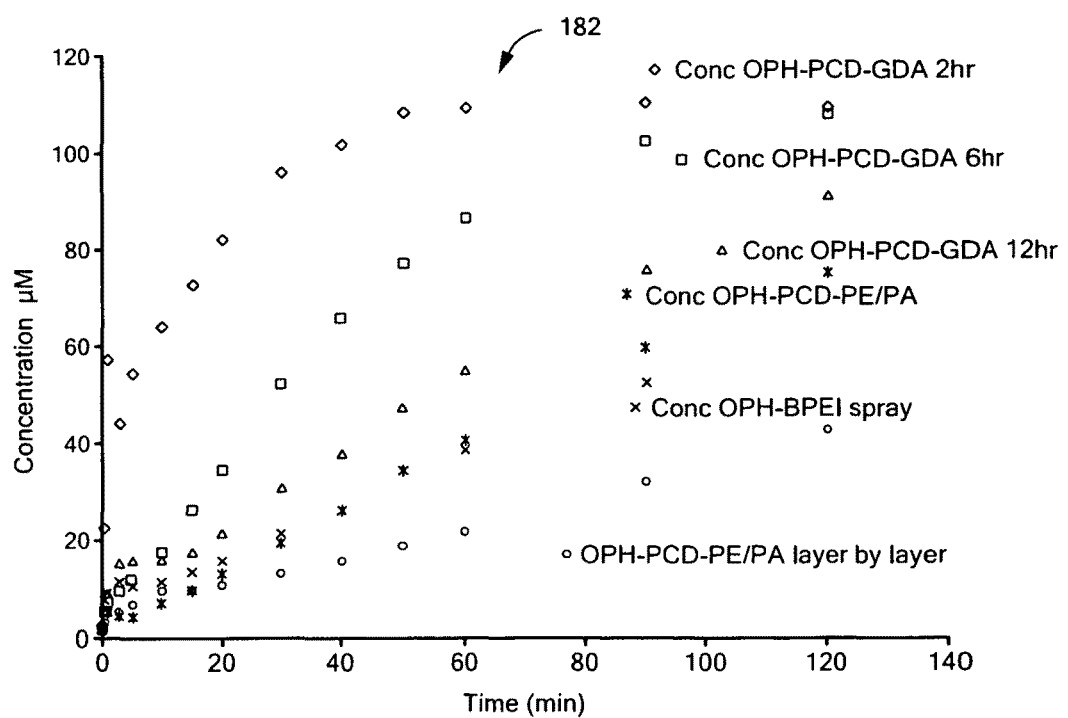
FIG. 18

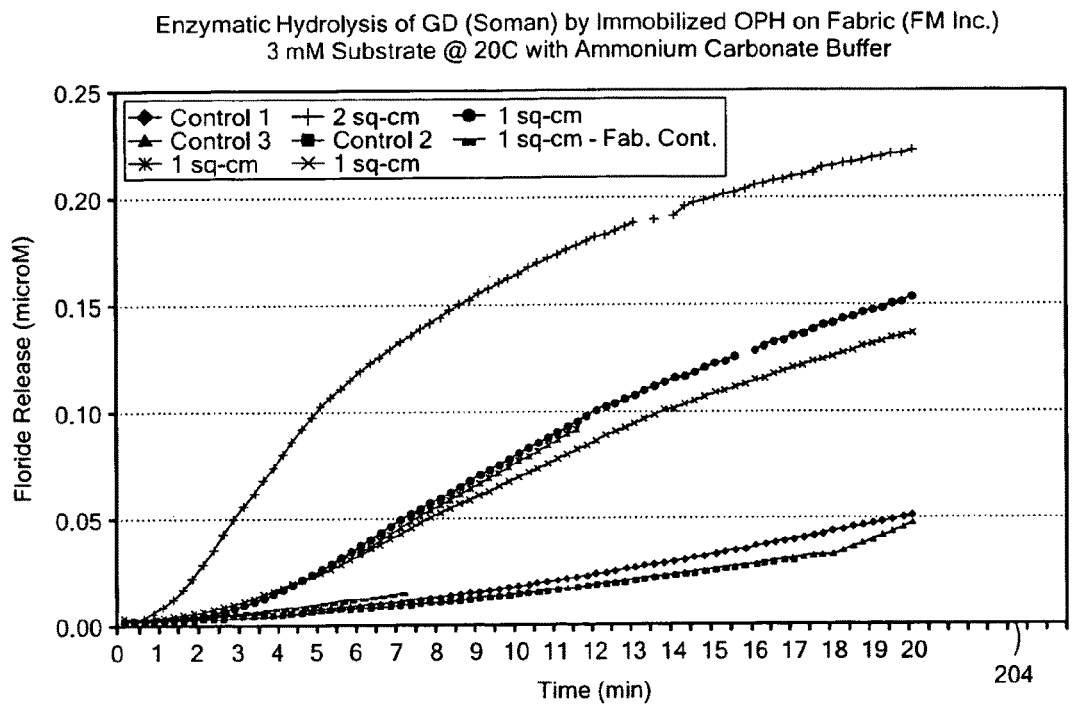

1. Control and OPH-immobilized fabric samples were analyzed by measuring hydrolysis of Soman and DFP, using acqueous phase testing.
2. Ammonium carbonate was used as a buffer and release of fluoride was measured in a final volume of 2.5 mL.
3. The assays were conducted at 20C with either 1 sq-cm or 2 sq-cm fabric piece.
4. The fluoride release exceeded the linear range of the electrode.
5. DFP was hydrolyzed in <1 minute.
6. GD (Soman) hydrolysis was >75% completed within 20 minutes with 2 sq-cm fabric sample.
7. Control fabric samples released <0.025 μM fluoride in 20 minutes.

*FIG. 20*

COATING SYSTEM COMPRISING SYNZYME FOR DEGRADATION OF THREAT AGENTS

RELATED APPLICATIONS

This application hereby claims the benefit of and priority to U.S. Provisional Application Ser. No. 61/281,900, filed on Nov. 24, 2009 under 35 U.S.C. §§119, 120, 363, 365, and 37 C.F.R. §1.55 and §1.78, incorporated by reference herein.

FIELD OF THE INVENTION

This invention relates to a sorption reinforced catalytic coating system and method for the degradation of threat agents.

BACKGROUND OF THE INVENTION

Chemical, Radiological, Biological and Nuclear Defense (CRBN) is a high priority of the Army and National Security due to rogue states and the rise of terrorist organizations that are technologically sophisticated, well-financed and committed to inflicting damage on U.S. interests and personnel. The increased threat of chemical and biological agent attack in various military theaters combined with the possibility of terrorist attacks on the general public has led the inventors hereof to evaluate protective equipment for military and civil defense. Battlefield chemical protective materials are sought that do not just serve as simple barriers to incoming threats, but can reactively decontaminate the threat agents so as not to impede the mission at hand.

It is known that an extremely small amount of a CWA, such as a nerve agent, can affect the transmission of chemical nerve impulses in humans leading to death soon after exposure. Because of this toxicity protection against CWAs, biological weapons and toxic industrial chemicals (TICs) requires capture efficiency greater than about 99.97 percent combined with sufficient decontaminating capabilities There are several known decontaminating technologies that have been developed to degrade CWAs and TICs. However, to date, there is no single solution to provide comprehensive protection for personnel working in both dry and wet environments.

One known chemical method typically employed to degrade stockpiles of CWAs uses caustic salts at high temperatures. However, such a method often generates side-reactions which can reverse to form the original toxic chemical agents. To overcome these shortcomings inorganic catalysts have been used to degrade CWAs and TICs because they are more robust but have low catalytic activity. More recently biological catalysts have been developed which rapidly and safely decontaminate CWAs or TICs but have limited life spans because of their fragile nature.

Enzymes, such as organophosphate degrading enzymes (OPH, OPAA), and the like, are reported to be efficient catalytic materials that effectively degrade CWAs and TICs. These enzymes denature rapidly when in solution and their performance is based solely on limited temperature and pH ranges. To mitigate these shortcomings the enzymes need to be immobilized, which will allow the system to be reusable, recyclable and recoverable while maintaining chemical activity towards all types of CWAs and TICs in both dry and wet environments.

Several known methods for immobilization of enzymes often rely on stabilizing the enzymes during the deposition phase and retard their deactivation upon prolonged exposure to stressful conditions. One known method relies on a covalent chemistry approach in which the reaction conditions use organic solvents. However, such a technique causes a major loss of enzyme activity. In one example, a research group developed a polyurethane nanosponge to degrade toxins. However, most of the enzymes incorporated into the sponge were eventually rendered inactive during the polymerization process.

To avoid such a loss of activity of the enzymes, one known layer-by-layer (LBL) method provides a versatile platform for the fabrication of multifunctional bio-materials utilizing catalytic enzymes. A Naval Research Laboratory (NRL) research team has reported enzymes immobilized in polyelectrolyte multilayer assemblies capable of maintaining their catalytic activity over long periods of time, e.g., greater than about 8 months. Fabricated OPH enzyme-bearing cotton cloths via layer-by-layer assembly preserved their hydrolytic activity against methyl parathion (MPT) within 5 minutes of exposure. The non-covalent method of the NRL team for incorporating enzymes helps tremendously in maintaining enzyme activity by protecting the enzyme from denaturizing. However, even this layer-by-layer approach has some distinct drawback. Many catalytic enzyme multilayers were shown to have limited activity towards their respective agents. This indicates only a limited amount of the enzyme, due to its amphoteric nature, was actually loaded onto the system.

BRIEF SUMMARY OF THE INVENTION

This invention features a sorption reinforced catalytic coating system for the degradation of threat agents including a synzyme coating about a material configured for the degradation of the threat agents, the synzyme coating including bucket-shaped molecules configured for the sorption of the threat agents. A binding agent is configured for synzyme immobilization to maximize loading and retention of the synzyme coating on the material.

In one embodiment, the bucket-shaped molecules may be configured to increase residence time of the threat agents in the synzyme coating. The bucket-shaped molecules may include cyclodextrin and derivatives thereof. The cyclodextrin and derivatives thereof may include β-cyclodextrin. The synzyme coating may include polyimine. The polyimine may be branched. The branched polyimine may include branched polyethylenimine (BPEI). The branched polyethylenimine may be functionalized with cyclodextrin and derivatives thereof. The branched polyethylenine may include amines which degrade the threat agents. The amines may include primary amines. The bucket-shaped molecules may include an inner hydrophobic pocket for attracting and increasing the residence time of the threat agents and for expelling hydrolytic degradation products of the threat agents. The binding agent may include aldehyde functionalized binders. The binding agent may include vaporous glutaraldehyde. The vaporous glutaraldehyde may be vaporized. The glutaraldehyde may be configured to selectively attach to the synzyme coating. The glutaraldehyde may selectively attach to free amines of a branched polyethylenimine. The free amines may include secondary amines. The glutaraldehyde may be configured to attach to the synzyme layer to prevent delamination. The glutaraldehyde may be configured to attach to the synzyme coating to render the synzyme coating insoluble in water. The vaporized binding agent may be configured to maximize loading of the synzyme coating on the material. The vaporized binding agent may be configured to provide for repeated cleaning cycles of the coating system. The binding agent may be configured to provide for reusability of the coating system. The synzyme coating may be configured to degrade the threat agents in a dry environment. The threat agents may include toxic industrial chemicals or warfare agents. The material may include fiber-based fabrics, meltblown nano based fabrics, electrospun nano fibers, cotton, or nylon.

This invention also features a method for making a sorption reinforced catalytic coating system for the degradation of threat agents, the method including coating a material with a synzyme configured for the degradation of the threat agents, the synzyme coating including bucket-shaped molecules configured for the sorption of the threat agents, and exposing the synzyme coating to a binding agent configured for the synzyme immobilization to maximize loading and retention of the synzyme layer on the material.

BRIEF DESCRIPTION OF THE SEVERAL VIEWS OF THE DRAWINGS

Other objects, features and advantages will occur to those skilled in the art from the following description of a preferred embodiment and the accompanying drawings, in which:

FIG. 15 depicts one example of the hypothetical catalytic process of β-CD-BPEI for the decontamination of the sarin (GB) toxin;

FIG. 18 depicts graphs showing one example of the decontamination kinetics of one embodiment of the sorption reinforced catalytic coating system for the degradation of threat agents of this invention employing an OPH enzyme-polymeric substrates at different time intervals;

FIG. 20 is a graph showing one example of the enzymatic hydrolysis of a Soman toxin exposed to one or more embodiments of the system and method of this invention employed on a meltblown fabric;

DETAILED DESCRIPTION OF THE INVENTION

Figure 1:
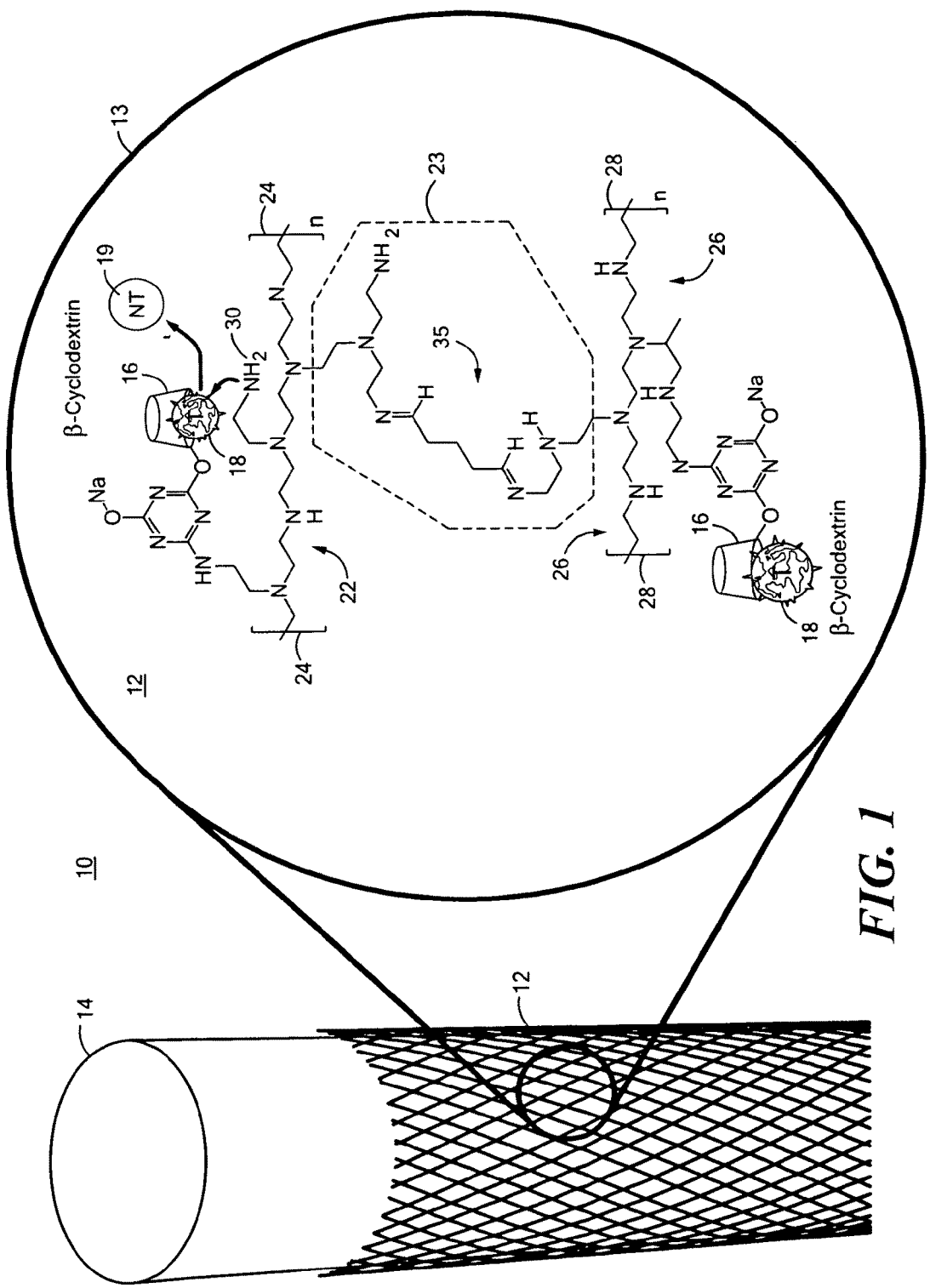
FIG. 1 is a three-dimensional view showing the primary components of one embodiment of the sorption reinforced catalytic coating system for the degradation of threat agents of this invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 2:
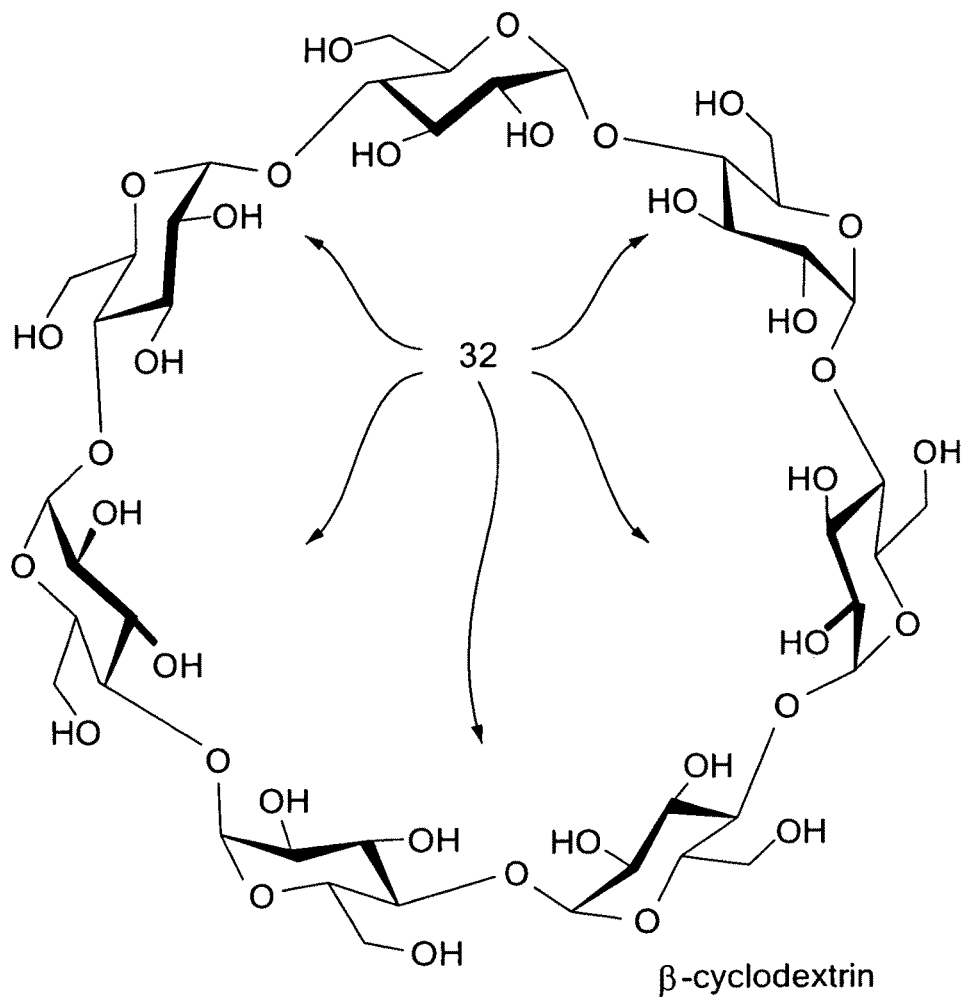
FIG. 2 is a depiction of the structure of β-cyclodextrin used in one embodiment of the system shown in FIG. 1.

There is shown in FIG. 1 one embodiment of sorption reinforced catalytic coating system 10 for the degradation of threat agents of this invention. System 10 includes synzyme coating 12 about material 14 (discussed below). Synzyme coating 12, shown in further detail in an exploded blowout 13, preferably includes bucket-shaped molecules 16 which provide for sorption of threat agents 18, e.g., CWAs, TICs, or similar type threat agents. In one example, bucket-shaped molecules 16 may include cyclodextrin derivatives thereof, e.g., β-cyclodextrin as shown in FIG. 2. Bucket-shaped molecules 16 may also include α-cyclodextrin, or any other similar type bucket-shaped molecules known to those skilled in the art. Bucket-shaped molecule 16 preferably increases the residence time of threat agents 18 in synzyme coating 12 which increases the efficiency of system 10 to degrade threat agents 18.

In one embodiment, synzyme coating 12 includes a polyimine which is preferably branched, e.g., branched polyethyleneimine (BPEI) or similar type of polyimine. For example, synzyme coating 12 may include BPEI having the chemical structure depicted by BPEI molecule 22 within brackets 24 and BPEI molecule 26 within brackets 28. BPEI is preferably functionalized with cyclodextrin and derivatives thereof, e.g., β-cyclodextrin, FIG. 2, α-cyclodextrin, or any other similar type bucket-shaped molecules known to those skilled in the art. The BPEI in synzyme coating 12, FIG. 1, preferably includes amines, e.g., primary amine 30 of BPEI molecule 22 which degrade threat agents 18.

Figure 4A:
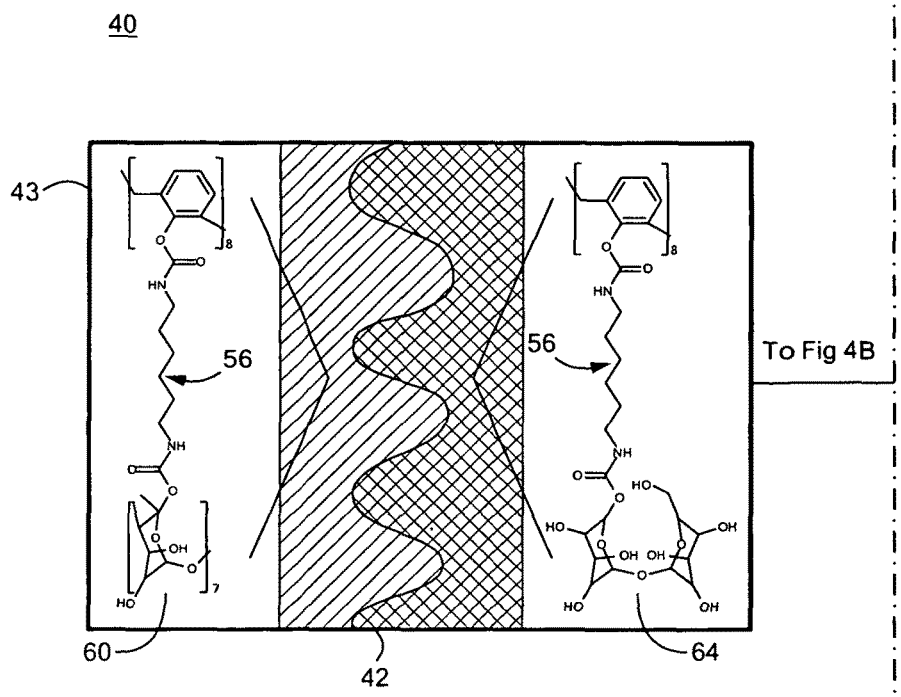
FIG. 4 is a three-dimensional view showing the primary components of another embodiment of the sorption reinforced catalytic coating system for the degradation of threat agents of this invention.
Figure 4B:
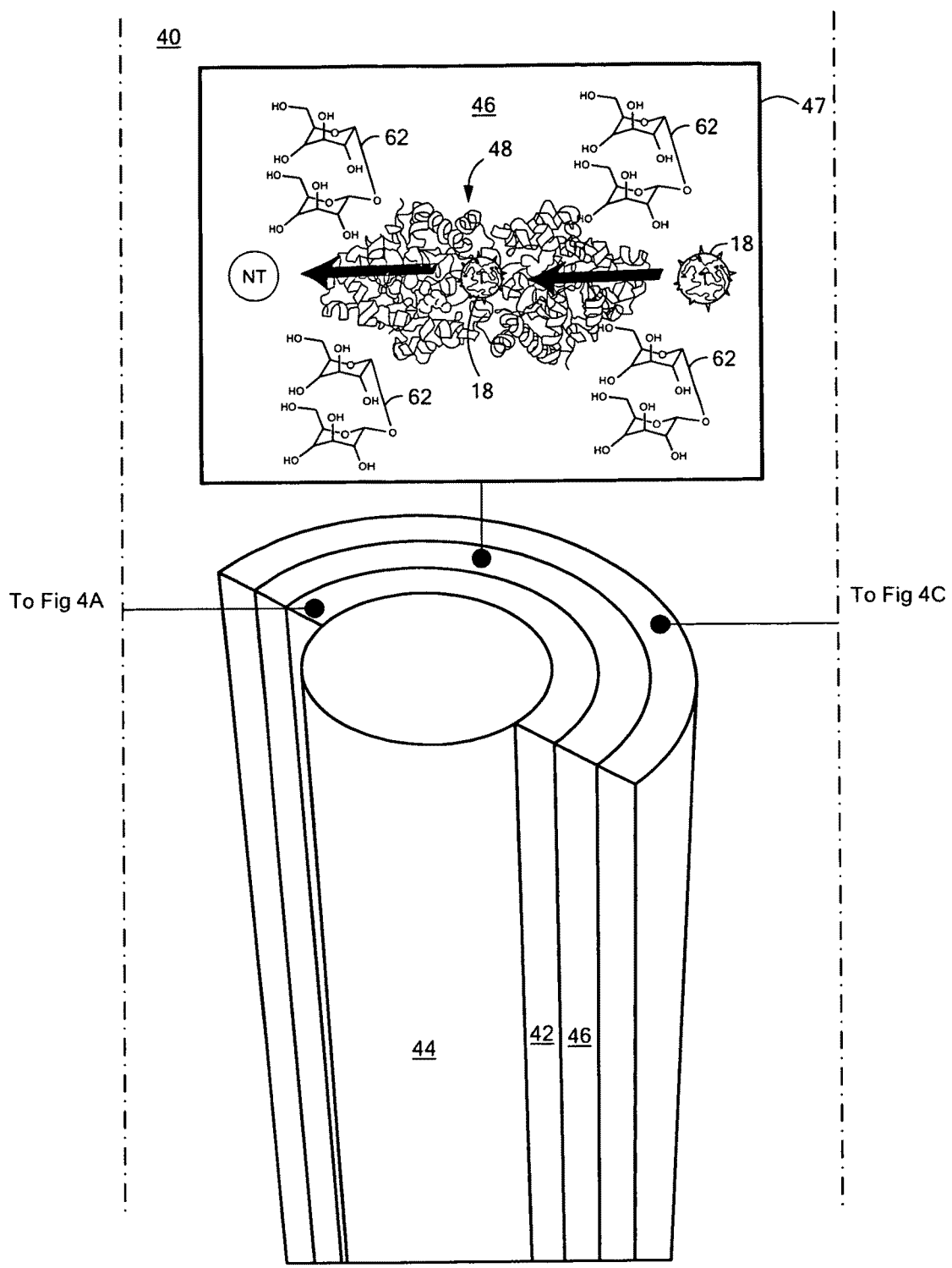
Figure 4C:
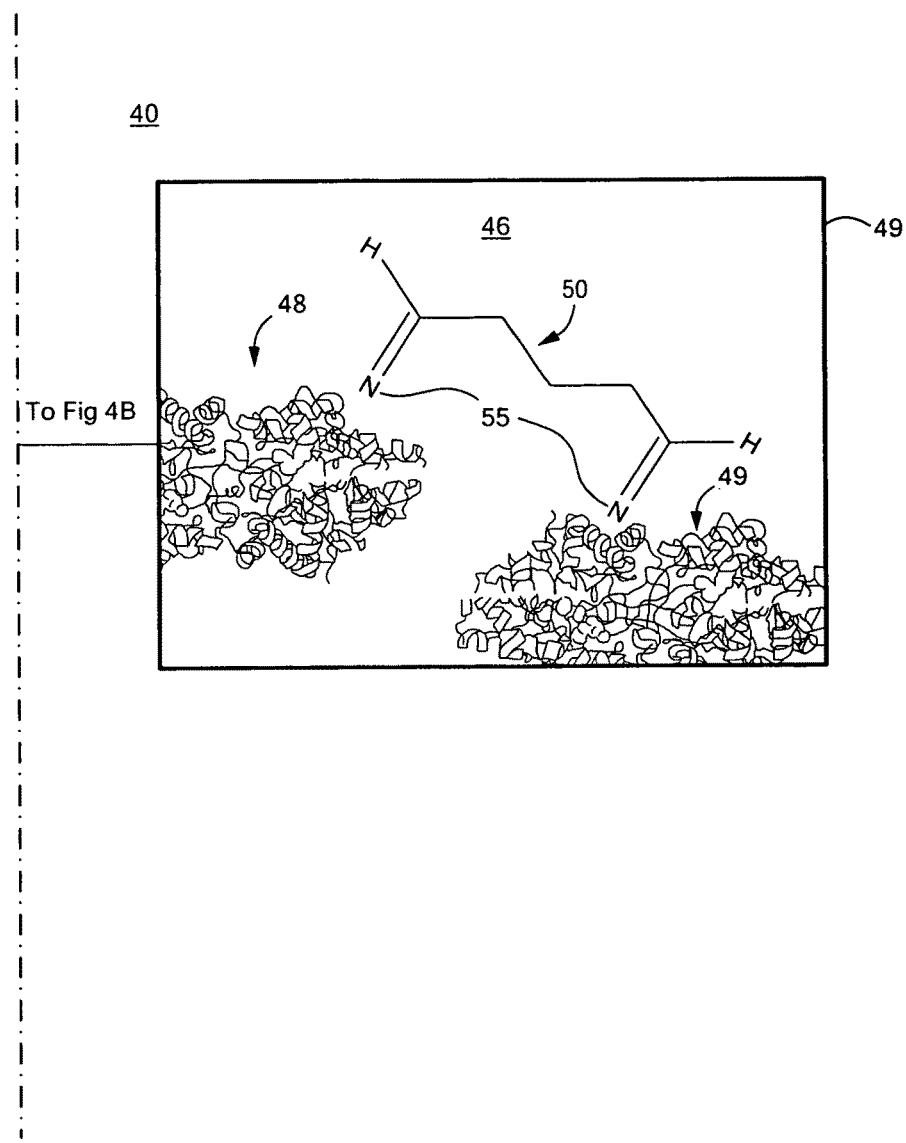
Figure 5:
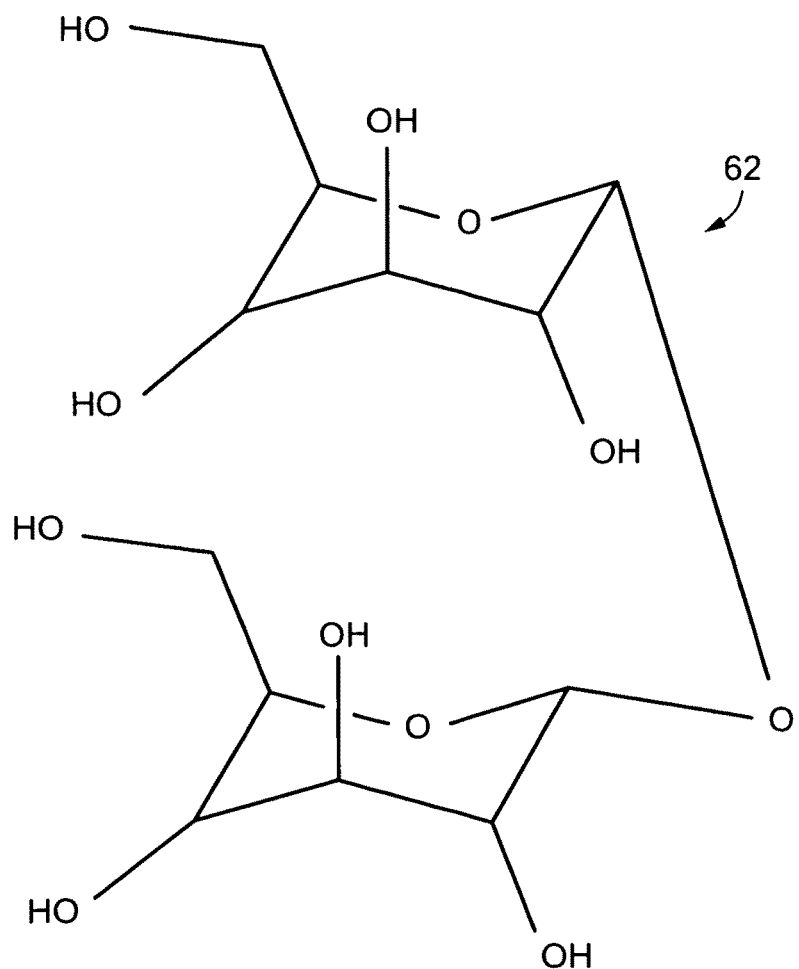
FIG. 5 is a depiction of the structure of trehalose which may be used in one embodiment of the system shown in FIG. 4.
Figure 6:
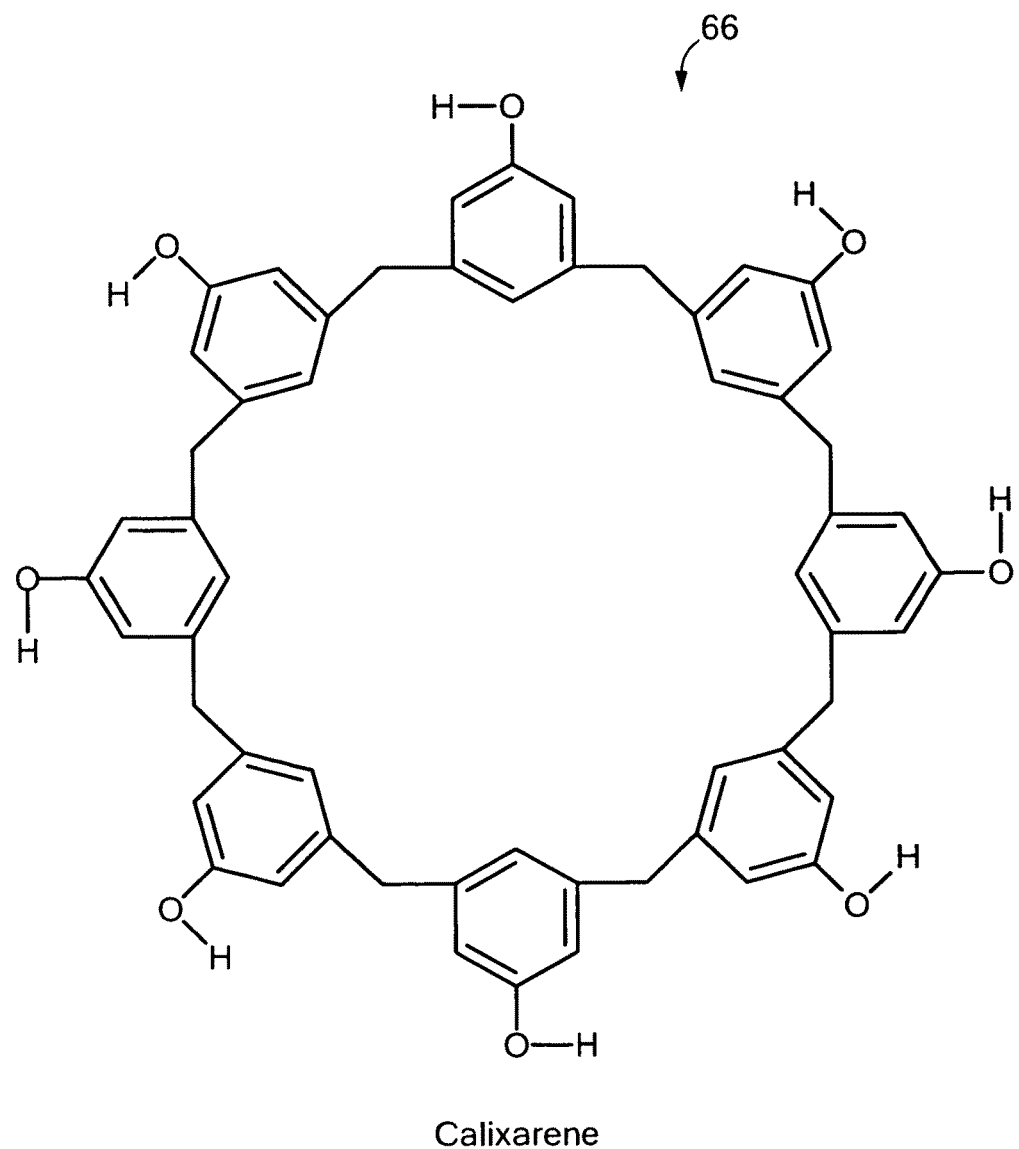
FIG. 6 is a depiction of the structure of calixarene which may be used in one embodiment of the system shown in FIG. 4.

In one example, bucket-shaped molecules 16 preferably include an inner hydrophobic pocket, e.g., inner hydrophobic pocket 30, FIG. 2, of β-cyclodextrin which attracts and increases the residence time of threat agents 18, FIG. 1, in synzyme coating 12 and expels hydrophilic degradation products 19 of the threat agents 18.

CWAs and TICs are typically hydrophobic. System 10 may overcome this problem by the introduction of the bucket-shaped molecules having a hydrophobic pocket, such as β-cyclodextrin and derivatives thereof which helps dissolution and extends the residence time of the CWAs and TICs via a host-guest complex formation. Through this interaction a more favorable homogenous environment is formed which allows for improved degradation of threat agents 18.

System 10 also includes a binding agent configured for synzyme immobilization to maximize loading and retention of synzyme coating 12 on material 14. Synzyme coating 12 on material 14 is preferably exposed to a vaporized binding agent then dried. In one example, the binding agent may be an aldehyde functionalized binder, such as glutaraldehyde (GA) 34, FIG. 3, and derivatives thereof, where R may be CHO (formyl), $CH_2OH$ (hydroxymethyl), $CH_2F$ (fluoromethyl), $CH_3$ (methyl), or $CH_2SH$ (mercaptomethyl). The binding agent, e.g., GA-34, selectively attaches to synzyme coating 12 to maximize the loading and retention of synzyme coating 12 to material 14. In one example, GA-34 (with the R as CHO), shown in its reacted state at 35 in box 23, selectively attaches to free amines of synzyme coating 12, e.g., secondary amines or primary amines of BPEI molecules 22, 26, respectively. The binding of BPEI molecules 22, 26 using GA-34 results in the structure indicated in dashed box 23.

Thus, the binding agent of system 10 maximizes loading and retention of synzyme coating 12 on material 14. This allows system 10, e.g., when utilized to make fiber-based fabrics such as those used in protective clothing or similar type articles, to withstand repeated cleaning cycles. The binding agent also prevents delamination of synzyme coating 12 which makes system 10 and the fabrics, protective clothing, articles, and the like, manufactured therefrom insoluble to water or similar type fluids. Thus, the protective clothing made using system 10 is reusable and recyclable. System 10 also effectively degrades threat agent 18 in a low moisture environment. Material 14 used by system 10 may include meltblown nano-based fabrics, electrospun nano fibers, cotton, nylon, and similar type materials.

Sorption reinforced catalytic coating system 40, FIG. 4, where like parts have been given like numbers, for the degradation of threat agents of another embodiment of this invention includes polyurethane coating 42 about material 44. Material 44 is preferably the same as material 14 discussed above. Polyurethane coating 42 provides for the attachment of one or more enzymes, e.g., enzyme 48 shown in block 47, and for the sorption of threat agents 18.

System 40 also includes enzyme coating 46 about polyurethane coating 42. Enzyme coating 46 includes one or more enzymes which degrade threat agents 18. In one example, enzyme coating 46 may include organophosphate degrading enzymes, such as organophosphorous hydrolase (OPH), organophosphorous acid anhydrolase (OPAA), and haloalkane dehalogenase (HD), or similar type organophosphate degrading enzymes. In the example shown in FIG. 4, enzyme 48 is a single OPH enzyme. Enzyme coating 46 may also include any type of enzyme known to those skilled in the art which can be used to degrade threat agents.

System 40 also includes a binding agent configured for enzyme immobilization to maximize loading and retention of the enzymes in enzyme coating 46 on material 44. Enzyme coating 46 on material 44 is preferably exposed to a vaporized binding agent then dried. Similar as discussed above with reference to FIGS. 1 and 3, the binding agent may be GA-34. In this embodiment, GA-34 (with R as CHO), shown in its reacted state at 50 in block 49, FIG. 4, selectively attaches to the enzymes of enzyme coating 46. In this example, the reacted GA-50 binds enzyme 48 (e.g., a single OPH enzyme) with enzyme 49 (e.g., another single OPH enzyme) to maximize the loading and retention of enzymes 48, 49 to enzyme coating 46 on material 44. The binding of the enzymes to each other on enzyme coating 46 using the binding agent may prevent system 40 from delaminating and makes system 40 insoluble in water. The result is system 40, e.g., when used to make fiber-based fabrics such as those used in, protective clothing, articles, and the like, as discussed above, may withstand repeated washings, may be recyclable, reusable and may effectively degrade threat agents 18 in a wet environment.

In one design, polyurethane coating 42, shown in greater detail in block 43, may be comprised of polyurethane backbone 56 which is functionalized with organic bucket-shaped molecules discussed above which stabilize the enzymes of enzyme coating 46. In one embodiment, polyurethane coating 42 may be functionalized with cyclodextrin and derivates thereof, e.g., β-cyclodextrin, FIG. 2, shown in this example functionalized to polyurethane coating backbone 56, FIG. 4, at 60. The bucket-shaped molecules may also include α-cyclodextrin or similar type bucket-shaped molecules which can be grafted onto the polyurethane coating 42 with sorptive capabilities. In this example, β-cyclodextrin stabilizes the enzymes of enzyme coating 46 by preventing the enzymes from conformational changes by secondary interactions, such as hydrogen bonding and hydrophobic interaction. β-cyclodextrin and the derivatives thereof may also effectively sorb threat agents 18.

Polyurethane coating 42 may also be functionalized with chemical groups that stabilize the enzymes of enzyme coating 46. For example, polyurethane coating 42 may be functionalized with sugar groups, such as trehalose 62, FIG. 5, shown functionalized to polyurethane coating backbone 56, FIG. 4 at 64 in block 43. Block 47 shows one example of enzyme coating 46 with a plurality of plurality of trehalose molecules 62 about enzyme 48 which stabilize enzyme 48. The functionalized polyurethane coating 42 with sugar group similarly prevents the enzymes in enzyme coating 46 from denaturing.

Polyurethane coating 42 may also be functionalized with calixarene 66, FIG. 6, and derivates thereof, which sorb radiological threat agents 18. Polyurethane coating 42, FIG. 4, may also be functionalized with chemical groups which promote water scavenging, e.g., trehalose 62, FIG. 5.

Similar, as discussed above with reference to FIG. 1, system 40 with material 44 may include fiber-based fabrics that may be used in protective clothing, various articles, and the like. In other examples, material 44 may include meltblown nano-based fabrics, electrospun nano fibers, cotton, nylon, and similar type materials.

Reinforced catalytic coating system 80, FIG. 7, where like parts have been given like numbers, is a combination of system 10, FIG. 1, and system 40, FIG. 4. In one embodiment, system 80 includes polyurethane coating 42 about material 44. Similar as discussed above with reference to FIG. 4, polyurethane coating 42 provides for the attachment of one or more enzymes and for the sorption of threat agents 18. Polyurethane coating 42 is preferably functionalized with organic bucket-shaped molecules discussed above which stabilize the enzymes of enzyme coating 46. System 40 also includes enzyme coating 46 about polyurethane coating 42 which, similar as discussed above, includes one or more enzymes which degrade threat agents 18.

System 80 also includes a first binding agent configured for enzyme immobilization to maximize loading and retention of the enzymes in enzyme coating 46 on polyurethane coating 42. Enzyme coating 46 on material 44 is preferably exposed to the first binding agent then dried. Similar as discussed above with reference to FIGS. 3 and 4, the first binding agent may be GA-34 which, in this example, is shown in its reacted state at 50, block 49, FIG. 7. The first binding agent selectively attaches to the enzymes of enzyme coating 46 and binds them together to maximize loading and retention of the enzymes in enzyme coating 46 on polyurethane coating 42.

Figure 7A:
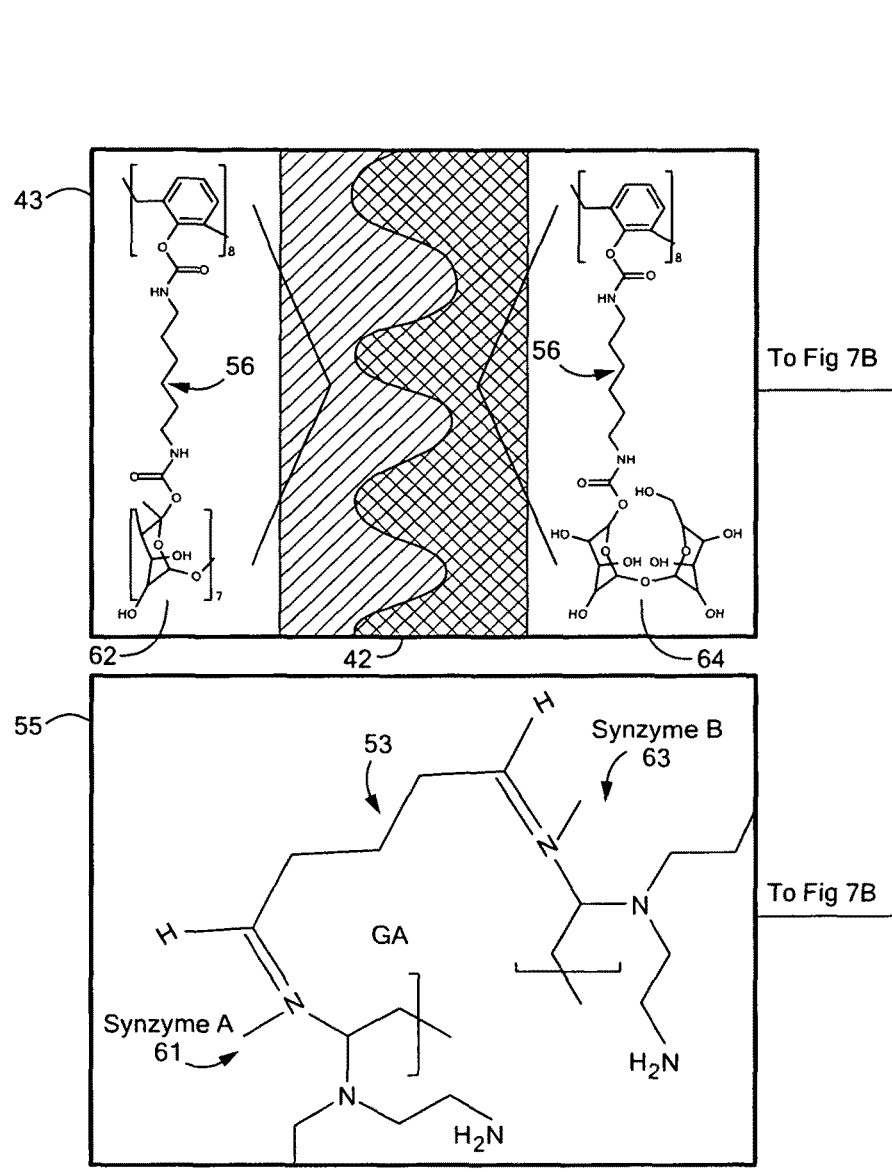
FIG. 7 is a three-dimensional view showing the primary components of yet another embodiment of the sorption reinforced catalytic coating system for the degradation of threat agents of this invention.
Figure 7B:
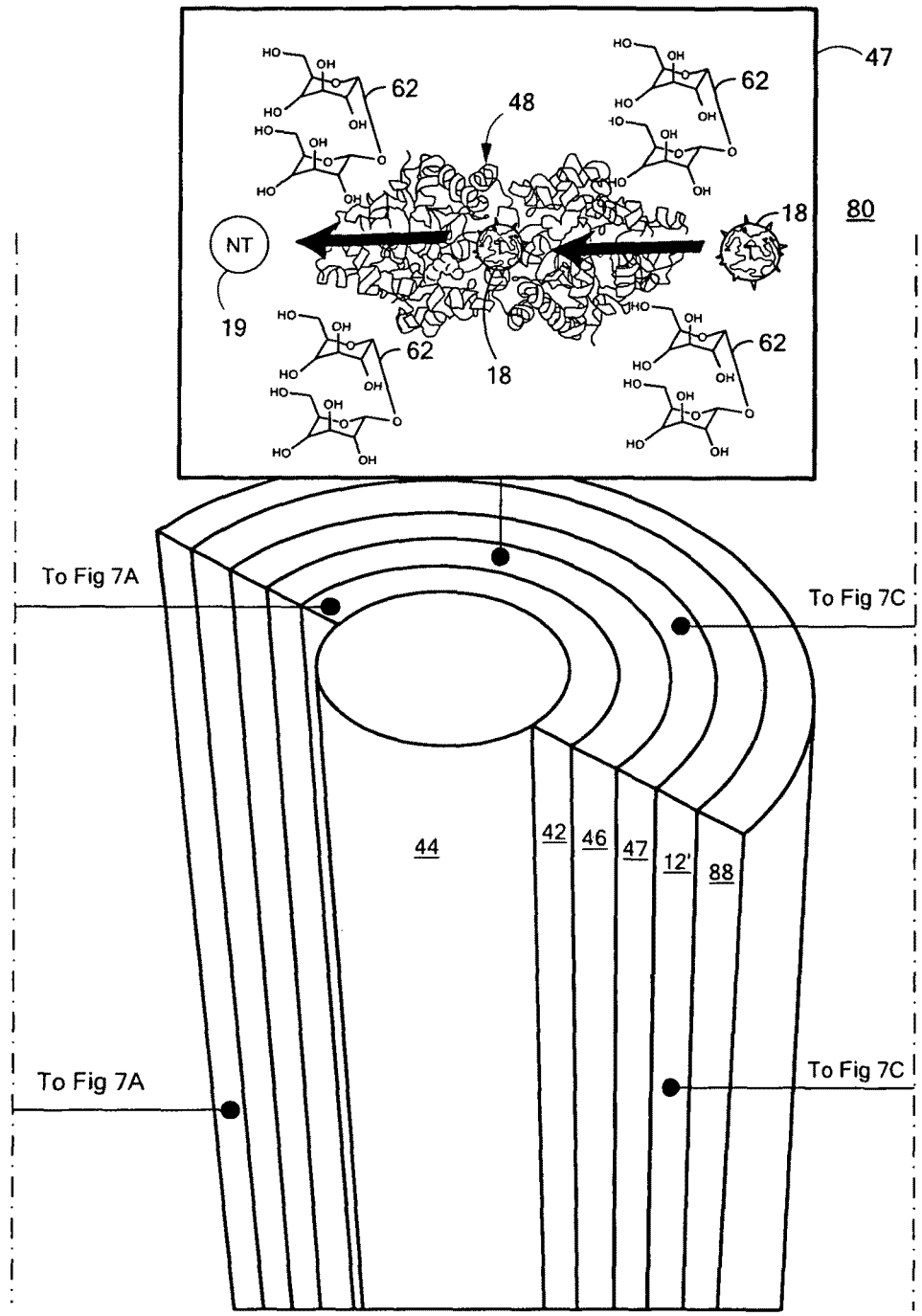
Figure 7C:
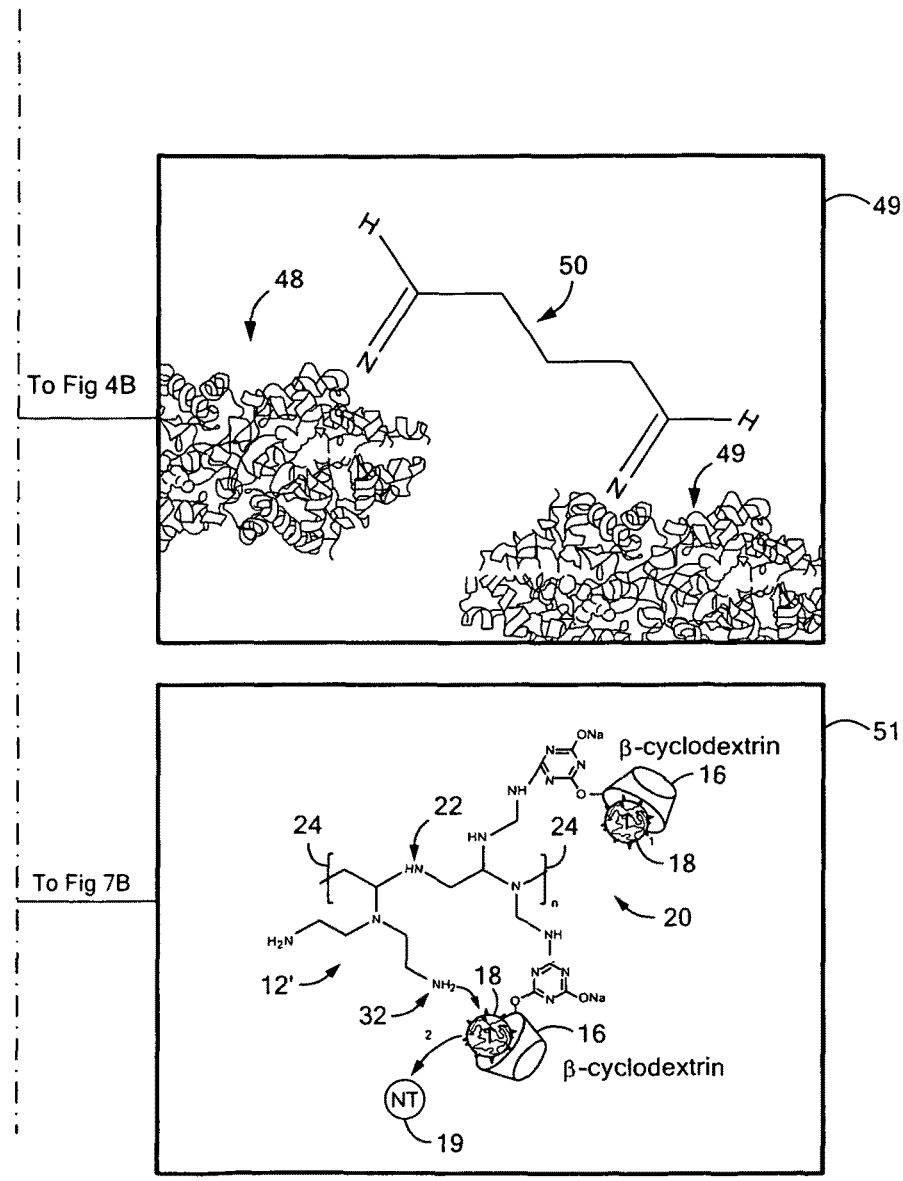

System 80 includes synzyme coating 12', shown in further detail in block 51, having a similar structure as synzyme coating 12, FIG. 1. However, in this embodiment, synzyme coating 12', FIG. 7, is disposed over enzyme coating 46 with the first binding agent. Synzyme coating 12' preferably includes bucket-shaped molecules which provide for sorption and degradation of threat agents, e.g., threat agents 18 shown in block 51, such as, CWAs, TICs, or similar type threat agents, as discussed above with reference to FIG. 1.

Figure 3:
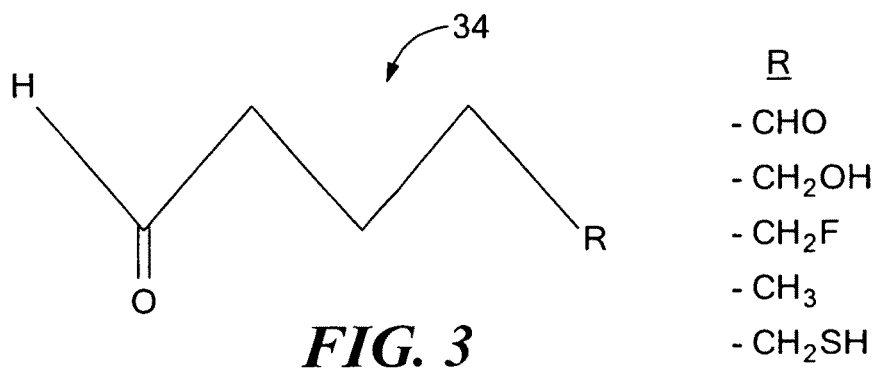
FIG. 3 shows one example of the structure of the binding agent shown in FIG. 1.

System 80, FIG. 7, also includes a second binding agent, e.g., GA-34, FIG. 3, having the structure in its reacted state shown at 53 in box 55, FIG. 7. Synzyme coating 12 on material 14 is preferably exposed as second binding agent then dried. The second binding agent is preferably configured for synzyme immobilization to maximize loading and retention of synzyme coating 12' on enzyme coating 46. In this example, the GA-53 has bound synzyme A-61 to synzyme B-63.

Figure 8:
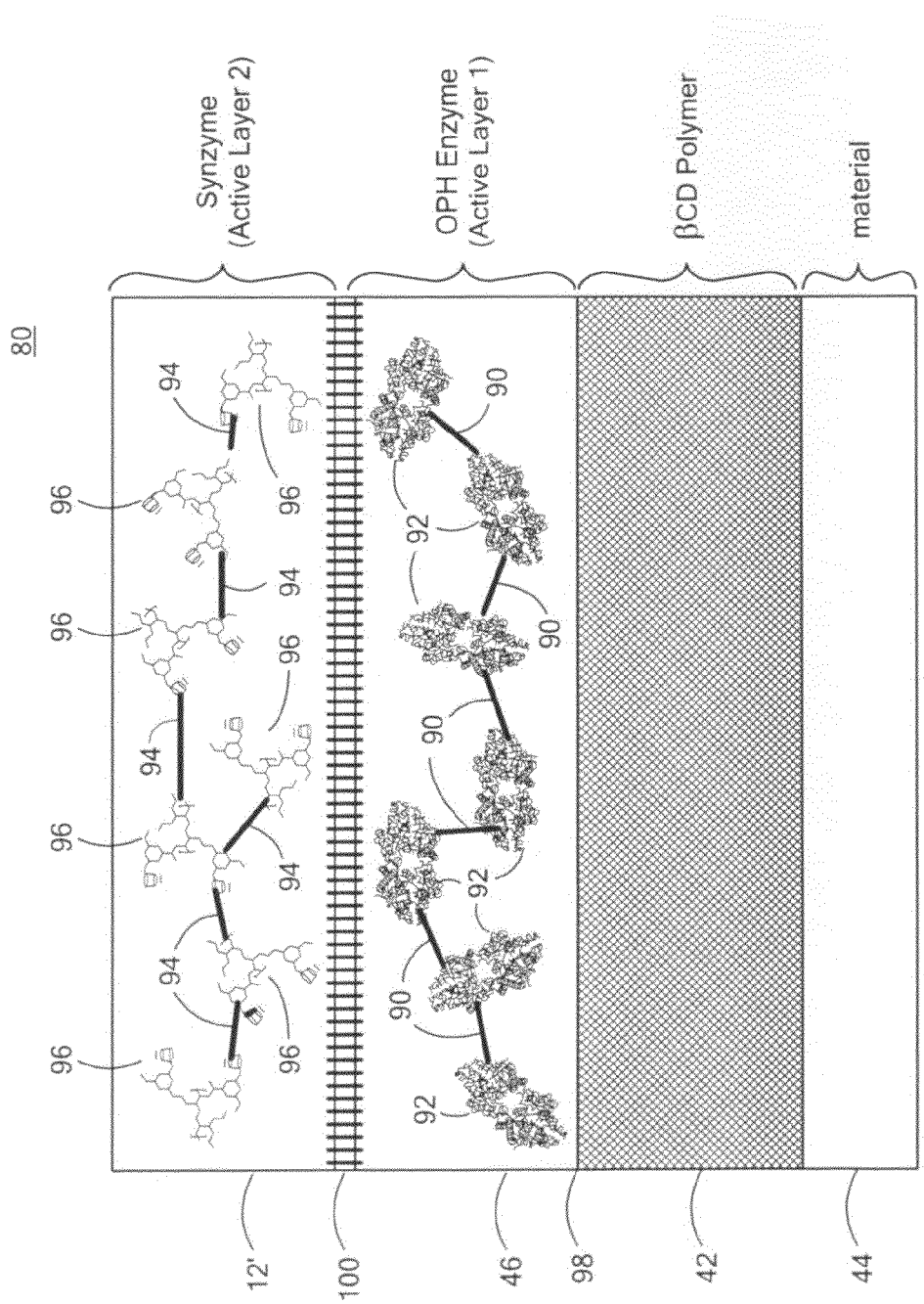
FIG. 8 is a schematic side view showing in further detail the various coatings and binding agents shown in FIG. 7.

FIG. 8 shows one example of one embodiment of the various coatings and binding agent of system 80: polyurethane coating 42 functionalized, in this example, with β-cyclodextrin on material 44, enzyme coating 46 with first binding agent, indicated at 90, binding enzymes 92, and synzyme coating 12' with the second binding agent, indicated at 94, binding synzyme molecules 96 together. Hydrogen bonding and/or hydrophobic interactions binds enzyme coating 46 to polyurethane coating 42, indicated at 98. The second binding agent also binds synzyme coating 12' to enzyme coating 46, indicated at 100.

The result is system 80 with polyurethane coating 42 on material 44, enzyme coating 46, the first binding agent which maximizes the loading and retention of the enzymes of the enzyme coating, synzyme coating 12' and the second binding agent which maximizes retention of synzyme coating 12' on enzyme coating 46 results in a system which includes all the features of the two embodiments discussed above with reference to FIGS. 1-6 into a comprehensive system which effectively degrades threat agents in both wet and dry environments. Thus, system 80 can be used to make fiber-based fabrics for protective clothing, various articles, and the like, that are insoluble to water, can withstand repeated washing, are recyclable and reusable, and do not delaminate.

EXAMPLES

The following examples are meant to illustrate and not limit the various embodiments of the present invention.

Novel sorption reinforced catalytic systems, capable of decontaminating CWAs and TICs, have been conceived and demonstrated.

These new catalytic systems and methods discussed herein may be based on enzyme bearing polymeric composites. These new systems have the added benefit of maximizing the enzyme loading while stabilizing the naturally fragile enzyme to maintain its catalytic activity by preventing its denaturing. Unique methods and compositional approaches that produce catalytic systems that chemically degrade CWA and TIC compounds in water and air have been demonstrated.

The systems and methods discussed herein create a robust absorptive enzyme support material from polymerizable prepolymers to safely harbor the enzyme while maintaining its catalytic activity against CWAs and TICs. Enzymes are easily denatured and maintaining their catalytic activity when supported on materials such as activated carbon has heretofore been quite challenging. The systems and methods of various embodiments of this invention may utilize pore forming prepolymers which can be employed as a non-carbon based catalytic supports for enzymes selected to cause CWA and TIC degradation. In the event that the enzymes do get denatured, the enzyme can be reactivated even after multiple exposure cycles when supported on the innovative coatings discussed above, e.g., such as polyurethane coating 42 including β-cyclodextrin (Poly-β-CD), trehalose (Poly-TH), and similar type materials.

The systems and methods discussed above with reference to FIGS. 1-9 may maximize loading and retention of catalytic enzymes by employing non-conventional vaporous glutaraldehyde (GA) and its derivatives thereof in a controlled manner. This helps prevent enzymes from leaching out of the catalytic system during routine operations, which is a common problem typically experienced in conventional catalytic systems. One or more embodiments of systems and methods of this invention include the ability to sequentially incorporate the active components into a material, such as a fiber-based fabric, to create a comprehensive enzyme polymeric catalytic system using a unique deposition and chemical modification protocol. These polymeric enzyme systems (particles and fabrics) may provide the basis for full protection fabrics and protective clothing and various articles for use against CWAs and TICs such as chemical (both nerve and blister) agents and microbial attack. These system and methods discussed herein not only absorb CWAs and TICs upon encounter, but they preferably produce only non-toxic chemicals as a result of the decontamination.

The methods and materials of the systems and methods of the various embodiments of this invention may be used to create a catalytic system that has enhanced activity, robustness, and reusability. The catalytic system may include a set number of coatings, or layers, built up on each other, each providing protection from a different set of threat targets. In one example, the system starts out with the formation of an inner polyurethane coating or layer consisting of β-cyclodextrin, trehalose, and calixarene. See, e.g., A. Singh, Yongwoo Lee, and Walter J. Dressick, *Advanced Materials*, 2004, vol. 16, pp 2112, incorporated by reference herein. This provides absorption towards CWA agents and TICs and acts as a stabilizing platform for catalytic enzymes. The cyclodextrin in this layer acts as an absorbent capturing CWA and TIC molecules into its hydrophobic bucket-shaped molecule and the calixarene has been shown to capture radiological waste particulates. Trehalose may be included as a stabilizer for the enzymes. Trehalose most likely provides stability by slowing down enzyme denaturation under stressful environments and as a moisture scavenger to deliver the necessary amount of water needed for the enzymatic decontamination reaction to occur. Once the polyurethane layer or coating is deposited, the biocatalyst layer may be placed onto the material, e.g., a fiber-based fabric. This layer preferably includes three decontaminating enzymes (e.g., OPH, OPAA and HD) preferably stabilized by monomeric trehalose and derivatives thereof. Once the enzymes are loaded, the entire system is exposed to vaporous GA for a period of time, which locks the enzymes into place while maintain their catalytic activity. Finally the system may be coated with chemically active polyethylenimine (PEI) and its derivatives thereof before being exposed to a second dose of vaporous GA to anchor the PEI to the system and lock everything into place. These two vaporous GA treatments allow for the safe incorporation of the individual layers onto the fabric substrate and prevent them from leaching out or becoming inactive during normal operations.

The systems and methods of the various embodiments of this invention are unique when compared to the currently available technologies. Two previous examples discussed in the Background section above for construction of enzymatic systems for the destruction of CWAs and TICs are LBL assembly and catalytic polymer nanosponge. The LBL system disclosed in U.S. Pat. No. 7,348,169, incorporated by reference herein, utilizes polyelectrolytes and natural polyionic interactions to build up layers of catalytic enzymes and counter polyelectrolytes sequentially. This system uses the natural attractions of oppositely charged species to build up the layers. This allows the catalytic material to be built up while retaining a relatively high percentage of catalytic activity in the final product. The main drawback of the LBL approach is that because it uses ionic interactions, the system is easily delaminated losing most, if not all, of its activity in a stressed environment. The NRL research team, inventors of U.S. Pat. No. 7,348,169, attempted to overcome this limitation by encasing the assembled catalyst structure with a polymer net. Further, only a limited amount of enzymes can be loaded in the layer-by-layer assembly. The second system developed by University of Pittsburgh utilizes organic solvents to polymerize their material in the presence of enzymes to create a nanosponge for catalytic degradation. But because the enzymes are exposed to organic solvents a vast majority of them become denatured and lose their activity. This greatly limits the catalytic ability of the catalyst system.

As compared to the catalytic systems discussed above, the system and methods of the various embodiments of this invention do not expose the enzymes to organic solvents and as such prevents their deactivation. Further, retention of the enzyme materials has been demonstrated through controlled usage of vaporous GA as a binding agent to permanently attach the enzymes and other active polymeric components onto the fabric, instead of using polyionic interactions. This results in greatly extended working life of our catalytic system.

Example I

Synzyme Coating

Amines are a well known group of weak nucleophilic compounds with a wide set of basic reactions which they participate in, but being relatively weak nucleophiles they are not capable of reacting with organophosphates and the like at ambient conditions, which requires a stronger nucleophile for a reaction to occur. But even with such limitations their chemical properties and reactivities can be changed by taking the monomeric amines and polymerizing them into chains which contain a large concentration of primary, secondary and tertiary amines. These new polymeric amines have been shown to exist in extensive branched networks. Branched polyethylenemine (BPEI), and shorter straight chain oligomeric amines, show an increased reactivity towards a wider spectrum of substrates. Once the amines are in this new polymerized form they have shown the ability to catalyze the hydrolysis of organophosphates without the amines themselves being used up in the reaction.

Laboratory experiments have shown that these amines, e.g., oligomeric and branched polyamines, have a new capability to react with organophosphates, such as Methyl Paraoxon (MPO) and Methyl Parathion (MPT), to generate p-Nitrophenol (pNP) which is less toxic then the original analyte. The sample preparation was minimal and the reactivity of the final product was evident almost as soon as the target agent was placed onto the material. It was also shown that these amines were not being consumed during the hydrolysis reaction, but only acting as a catalyst. This may be referred to as a synthetic enzyme or "synzyme".

A starting solution of the synzyme coating containing branched polyethyleneimine (BPEI) or a different oligomeric amine, and cyclodextrin bearing branched polyethyleneimine (CD-BPEI) was made by dissolving it in deionized (DI) water at a concentration of 10 mg/mL. After the BPEI/oligomeric amine, and cyclodextrin bearing branched polyethyleneimine (CD-BPEI) was completely dissolved, a fabric sample (cotton, Polyester/Polyamide (PE/PA)) was coated with the resulting solution. The coating was done in 1 of 2 ways: (1) The sample was forcefully impregnated by squeezing the synzyme solution into the fabric until it was saturated or (2) by spraying the synzyme solution with an atomizer onto the fabric sample until it was completely covered and allowing it to naturally impregnate the fabric. After the sample was coated it was allowed to dry. The drying was also performed in one of two ways: (1) the sample was frozen and lyophilized or (2) the sample was allowed to air dry by the use of air dryers. Both methods produced samples showing the same rate of reaction.

Figure 9:
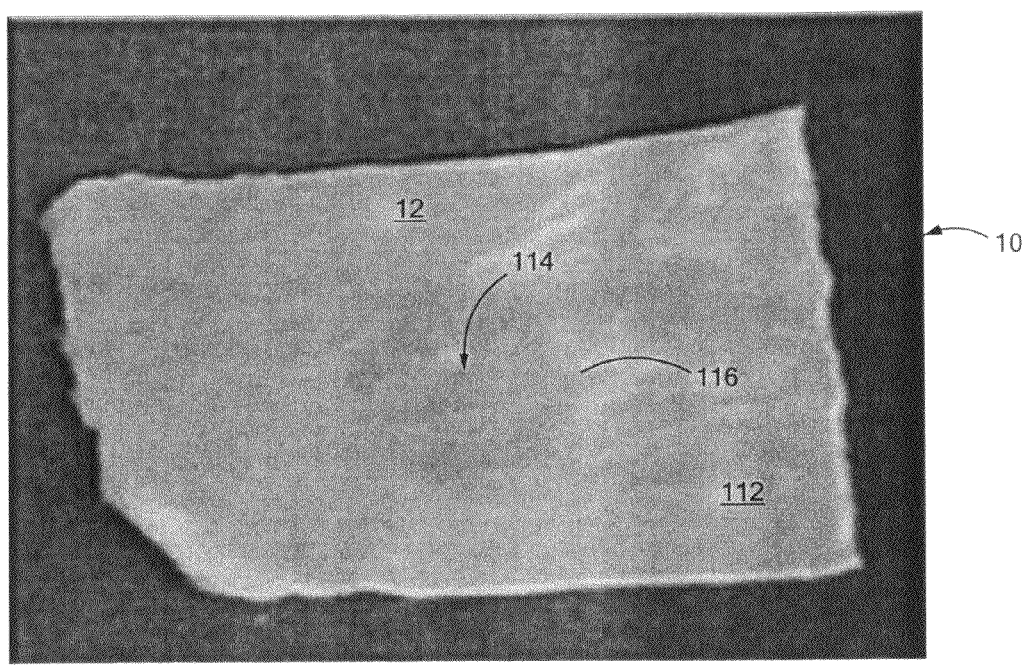
FIG. 9 is a photograph showing one example of the synzyme coating of one embodiment of this invention coated on a fabric and being exposed to a colorless methylparaoxon (MPO) toxin and showing the development of a distinctive yellow color of the p-Nitrophenol (pNP degradation by-products)

Once the samples were ready they were tested against Methyl paraoxon (MPO) an organophosphate compound. In one example, testing was performed by placing a neat drop of the colorless MPO onto the synzyme coating 12 of system 10, discussed above with reference to FIGS. 1-3, coated on fabric sample and allowing it to react with the coated material. The test results of this example are shown in FIG. 9. As shown, white cotton fabric 112 was coated with the synzyme solution consisting of BPEI and CD-BPEI followed by GA binding. After drying the fabric sample, a drop of MPO, which is clear, was placed onto fabric 112 at the area indicated at 114. After exposure the sample developed a distinct yellow color, shown at 116. This is characteristic of the hydrolysis product, p-nitrophenol (pNP). The sample was then extracted using MeOH and the resulting solutions were analyzed using UV-VIS to conclusively prove the presence of pNP by its distinctive peak at 405 nm, as compared to the MPO peak at 275 nm.

One issue which arises with the use of the BPEI is its inability to hold onto a chemical analyte long enough to allow the hydrolysis reaction to occur, limiting its chemical activity. In order to increase this activity a system to increase the residence time of a target compound near the active site was developed. This was achieved through the utilization of a polycyclic compound (Cyclodextrin (CD)), as discussed above with reference to FIG. 1, which possesses a hydrophobic pocket which can accept organophosphates through a guest-host complex formation. This combination of the reactive amine backbone and the retentive CD provides a dual attack strategy for not only reversibly capturing organophosphates, and other similar compounds, but also for its hydrolysis into less toxic products.

While the reaction rate could be easily increased by the addition of the CD there was a second issue with using this as a reactive coating: The reactive coating's dessolution in water. This issue was overcome by cross-linking the amine chains after deposition onto a substrate which prevents its delamination. The simplest cross-linking agent used was a dialdehyde compound, Glutaraldehyde (GA), which is highly reactive to amines. But it was also this reactivity which had to be controlled. If a solution of GA was to be exposed to a synzyme coated fabric, the resulting exhaustive cross-linking would make the final product very brittle. This brittleness could be overcome by limiting the exposure of the GA to the fabric, which can be achieved by exposing the coated fabric to only the fumes of GA (vaporized GA). The fumes provide enough active material to prevent the delamination of the BPEI coating but it prevents the extensive cross-linking which would lead to a brittle product. Another manner of controlling the amount of GA cross-linking would be to use a solution containing a mixture of monoaldehyde compounds along with GA. This prevents a complete cross-liking and prevents the material from becoming brittle.

The field of synthetic enzymes, or "enzyme mimics", is currently under investigation. For example, the publication "An 'Artificial Enzyme' Combining a Metal Catalytic Group and a Hydrophobic Binging Cavity" by Ronald Breslow and Larry E. Overman, J. Am. Chem. Soc., 92 (4), 1075-1077 (1970), incorporated by reference herein, discloses utilizing cycloexaamylose as a hydrophobic core provider to increase the residence time of simple organic compounds to allow them to react with a metal based catalyst. In another publication "High Rates and Substrate Selectivities in Water by Polyvinylimidazoles as Transaminase Enzyme Mimics with Hydrophobically Bound Pyridoxamine Derivatives as Coenzyme Mimics," by Rachid Skouta, Sujun Wei and Ronald Breslow, J. A. Chem. Soc. 131, 15604-15605, (2009), incorporated by reference herein, discloses using a polymer which contained polyaziridines to convert phenylpyruvic acid into phenylalanine in water, with an increase in the reaction rate of $3.5 \times 10^5$ when compared to the reaction performed in water with no polymer present.

Example II

Sorption Reinforced Self-Decontaminating Polymeric Bio-Catalytic System Against Chemical Warfare Agents (CWA)

One purpose of one or more embodiments of this invention is to develop sorption-reinforced, self-decontaminating enzyme-polymeric coatings for military uniforms (fabrics imbedded with particles) capable of providing comprehensive protection at low and high temperatures against nerve, blister and microbial agents. Currently no known enzyme catalytic system is available which allows for: 1) recycled use through self-repairing (refolding) technology, 2) to decontaminate chemical agents followed by subsequent sequestering of break down products for safe disposal, 3) protection against blister agents (sulfur mustard) without producing geno-toxic intermediates, and 4) increased protection by maximizing the loading and locking of catalytic enzymes and nucleophilic polymers at low temperature environments (4° C.) as well as at ambient conditions. The system and method of one or more embodiments of this invention provides an efficiently decontaminating catalytic system which is highly compatible with absorptive activated carbons and other decontaminating technologies, and may be capable of providing comprehensive protection against chemical nerve and blister agents.

In one example, biocatalyst components are embedded into the fabric which can protect against both nerve and blister agents. There is no known efficient catalytic system that can decontaminate all classes of chemical agents, while at the same time allowing for safe subsequent disposal of the agents' reaction products, and that can be recycled through self-repair (i.e., enzyme refolding technology), and which protects against sulfur mustard or similar CWAs and TICs without the formation of genotoxic intermediates. Active enzymes were sequentially incorporated into particles and ultimately into fabric using non-covalent self-assembly to create a comprehensive catalytic system. It was demonstrated that the enzymatic system was capable of rapid response to and degradation of simulant challenges and was capable of self-repair over multiple challenge cycles. The use of three fast acting decontaminating enzymes (e.g., OPH, OPAA, and HD) incorporated onto a polymeric substrate (particles and fabrics) as the self-decontaminating, self-repairing, antimicrobial polymeric enzyme system highly catalytic not only at ambient conditions but also at near-freezing temperatures. The enzyme-bearing polymeric substrates (particle and fabrics) typically consist of four components. The catalytic enzymes are bound in a non-covalent fashion to the absorptive polymeric support via physisorption and then locked-in with the use of vaporous glutaraldehyde (GA) and thereby tuned favorably in the local microenvironment. Preferably, β-CD-BPEI is positioned at the outermost surface as a capping layer in the sorption reinforced self-decontaminating system.

Absorptive polymeric substrates have been prepared not only for absorbing chemical agents by inclusion complex formation, but also for acting as insoluble supports to harbor enzymes safely. As a supporting material of the OPH enzyme in the catalytic system of this invention, polyurethane-β-cyclodextrins (PU-β-CD) and polyurethane-trehalose (PU-TH) are used due to their sorption capabilities. These supporting materials are also flame-retardant, antimicrobial, catalytic in ester hydrolysis and capable of forcing chemical species into their cavities through hydrophobic interactions. In that manner, both PU-β-CD and PU-TH can sequester chemical agents.

Part I: Ultrathin, Compact Self-Decontaminating Catalytic Bio-Polymeric System

The sorption reinforced catalytic system for the degradation of threat agents of one or more embodiments of this invention are preferably non-toxic, non-corrosive, non-flammable, environmentally safe and highly compatible with a number of different enzymes. Performance was reproducible and the system and methods have been shown to be reusable, based upon testing against Soman (GD), Sarin (GB) and diisopropylfluorophosphate (DFP) in a closed working environment and in open air. In one example, the system and methods of one or more embodiments of this invention discussed above, was stressed using Chlorox brand bleach, organic solvent (methanol) and 1M HCl solution showing a retention of 40%, 35% and 18% of original activity, respectively.

The sorption reinforced catalytic system and method for the degradation of threat agents of one or more embodiments of this invention is recyclable and may be based upon the concept that decontamination occurs only in homogeneous local environments when chemical warfare agents (CWAs) and TICs get in contact with reactive species. CWAs and TICs are typically hydrophobic. This may be overcome by the introduction of hydrophobic bucket-shaped β-cyclodextrin, which helps extend the residence time of the CWA molecule in the system through host-guest complex formation. Through this interaction a more favorable homogenous environment is formed allowing for the degradation of the hydrophobic chemical agent.

Activated carbon absorbs almost all pollutants indiscriminately but is not recyclable. This leads ultimately to irreversible random attachment which might block the reactive site of catalysts immobilized and thus prevents its easy access to supply anionic hydroxyl or amine groups, essential for hydrolytic degradation of pollutants.

The systems and methods of one or more embodiments of this invention are not intended to create hypersorptive materials like activated carbons. Instead, absorptive recyclable polymeric matrixes are created which favorably harbor and stabilize enzymes by avoiding multi-point attachment, and maximize the residence time of incoming CWAs and TICs within the bucket-shaped cyclodextrin pores to allow enough time for them to be degraded by the active layers of enzymes and nucleophilic β-CD-polyethyleneimine (BPEI). The hydrophobic CWAs and TICs can be degraded into smaller and less toxic hydrophilic by-products. Those absorptive pre-polymeric materials can be easily created on fabrics at ambient conditions simply by dipping the pre-polymerized organic solvent mixture of β-cyclodextrin, hydroxypropyl β-cyclodextrin, calix[4]arene, calix[6]arene, calix[8]arenes, and spacers of hexyl diisocyanates (HDI) in DMF solvent.

Figure 10:
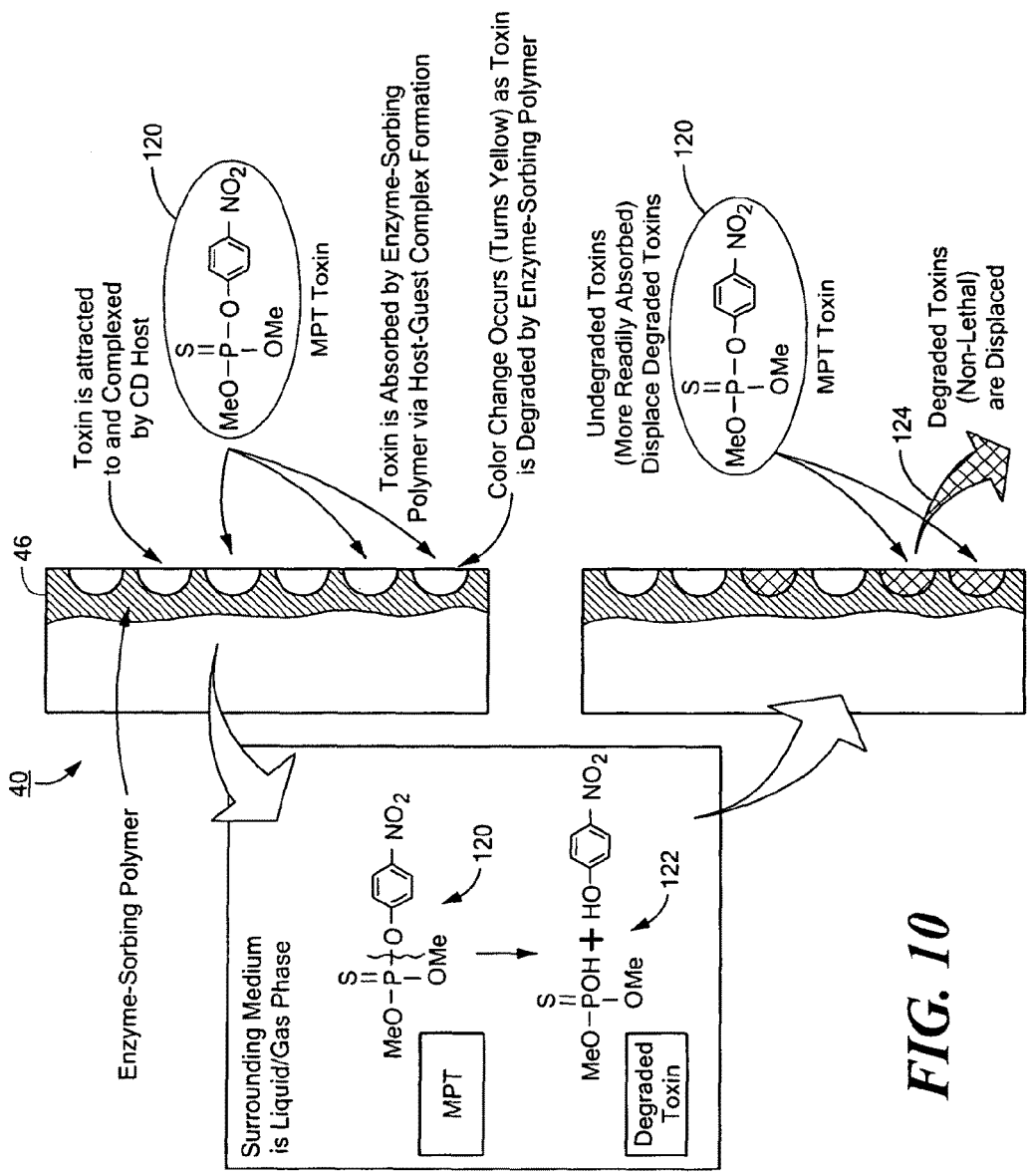
FIG. 10 is a schematic side view of one embodiment of sorption reinforced catalytic coating system of this invention showing in further detail one example of an enzyme coating degrading a MPT toxin to produce degraded non-lethal by-products.

Once CWAs and/or TICs come in contact with OPH-PU-β-CD, they get adsorbed to the ultrathin outermost surface where both catalytic hydrolysis and nucleophilic substitution occur. Following the degradation of the chemical agent, it's now hydrophilic byproducts are repelled from the hydrophobic β-cyclodextrin interior and captured by tertiary (3°) amines present in the system of one or more embodiments of this invention, freeing the active site for another incoming CWAs and TICs molecules. This cycling allows for the continual capture, degradation and sequestering of by-products for safe disposal at a specifically designated time by the user. FIG. 10 shows one example of MPT toxin 120 degraded by enzyme coating 46 of system 40 discussed above with reference to FIGS. 4-6 to produce the degraded toxin pNP 122 which is expelled from coating 46, as shown at 124.

Part II: Development of Absorptive and Nucleophilic Polyurethane Involving the Pore-Forming Building Blocks Building blocks of the sorption reinforced catalytic system and method for the degradation of threat agents of one or more embodiments of this invention is now discussed. In one example, co-polymeric polyurethanes were produced in-situ in the presence of pore-forming β-CD to stabilize/retain specific enzymes of interest by host-guest complex formation. Hydrolytic enzymes are employed to degrade CWAs and TICs. Branched polyethylene imines and oligomeric imines are used to degrade and sequester CWAs and TICs and their subsequent by-products: nucleophilic catalytic primary imines pointing towards the air ready to react with incoming toxins, secondary imines used in cross linking for permanent attachment to the fabric substrate, and tertiary imines utilized as an active site to capture degraded by-products. β-cyclodextrins embedded throughout the system act as hosts to capture toxins before eventually releasing then for decontamination. The entire system also shows antimicrobial activity, but actual active species is not known as the individual components show no activity before coating.

II-1-1: Absorptive Polyurethane-β-Cyclodextrins (PU-β-CD): Preferential Absorption of Hydrophobic MPT Over Hydrophilic pNP β-cyclodextrin and its derivatives are known to have exceptional absorption capabilities against TICs including CWAs. Los Alamos National Laboratory researchers developed a new class of organic nanoporous polyurethane sponge (0.7-1.2 nm) using β-cyclodextrin as a building block. These nanoporous polymers demonstrate excellent absorption capability against TICs in water. According to the report, hazardous organic contaminants may be reduced to ppt levels in water by these nanosponges.

Figure 11:
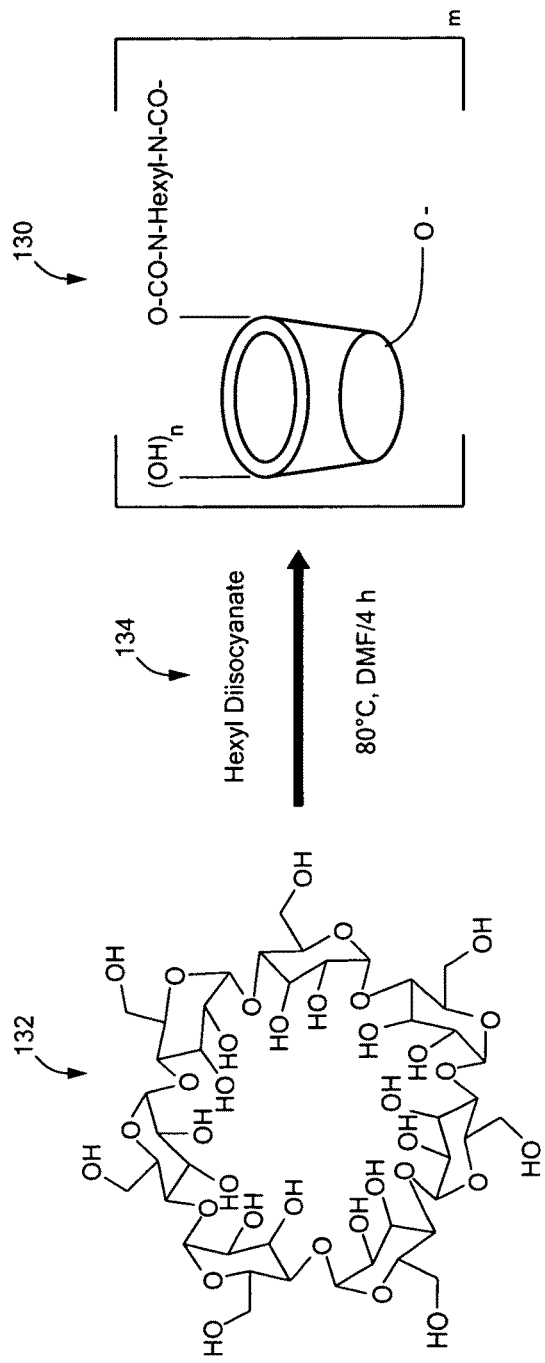
FIG. 11 shows one example of the preparation of polyurethane-β-Cyclodextrin (Poly-β-CD) using exhaustive cross-linking of β-CD.

In one example, polyurethane-β-cyclodextrin 130, FIG. 11, (PU-β-CD) was prepared by exhaustive cross-linking of β-cyclodextrin 132 with a spacer 134. According to published results and our experimental data, exhaustive cross-linking of cyclodextrin derivatives with excessive amounts of alkyl spacers was not the method to generate the highly absorptive material with high surface area.

Figure 12:
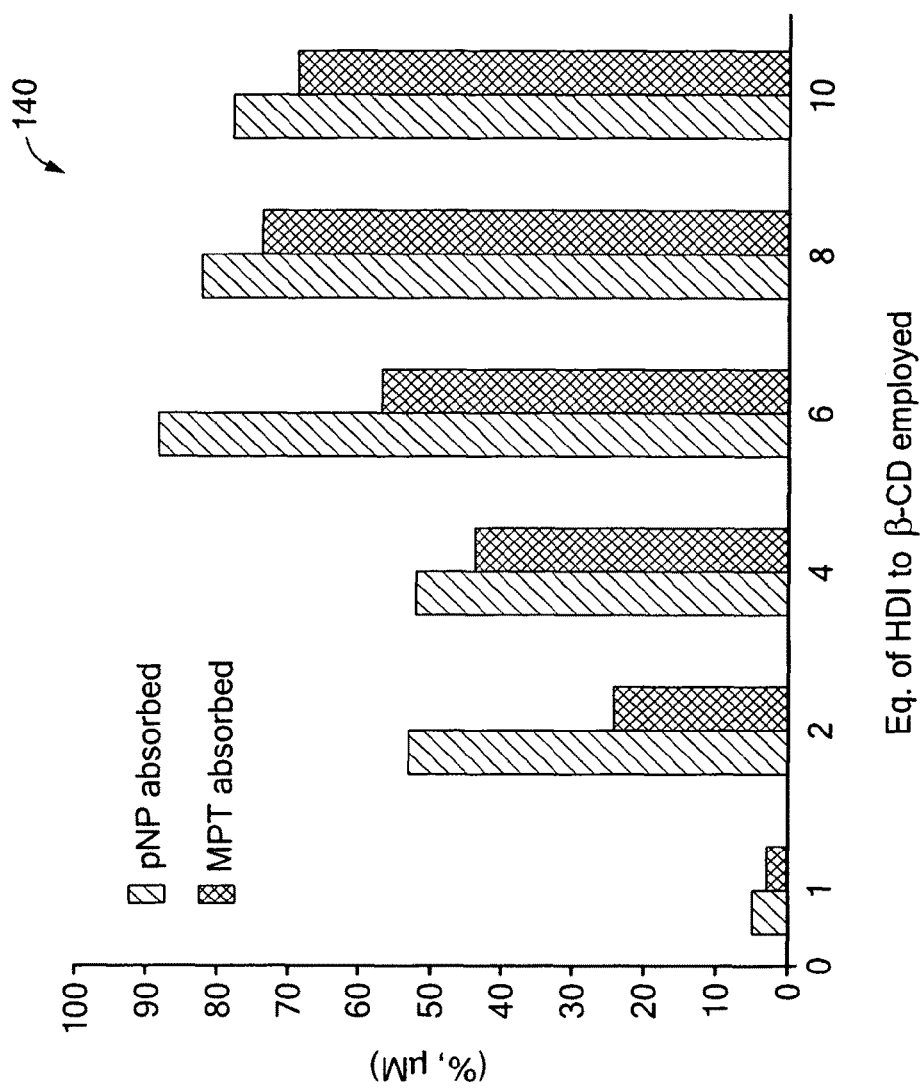
FIG. 12 is a graph showing one example of the absorption behavior of a cotton thread coated with a Poly-β-CD in accordance with one or more embodiments of this invention.
Figure 13:
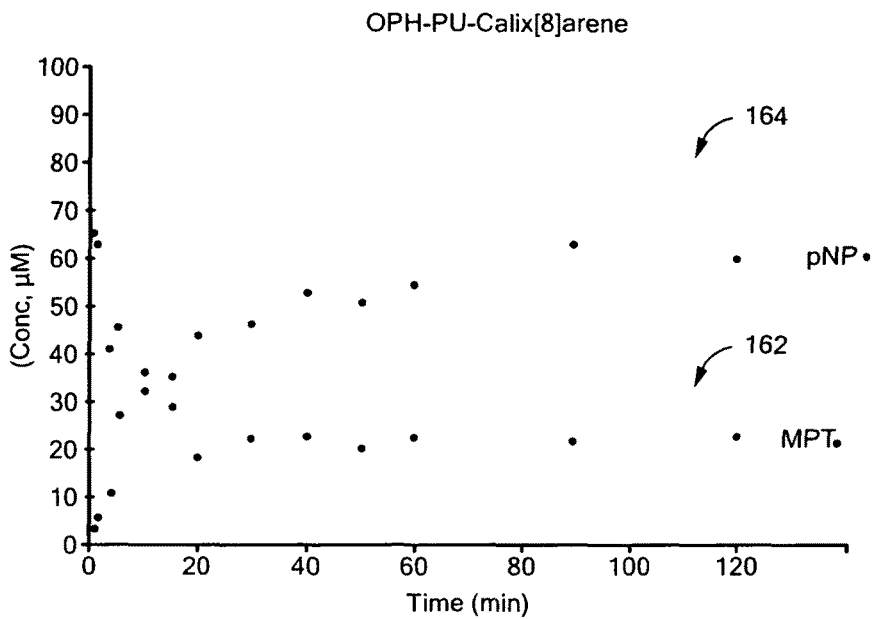
FIG. 13 shows graphs depicting an enzyme coating with an OPH coated PU-CX particles degrading MPT to pNP in accordance with one or more embodiments of this invention.
Figure 14:
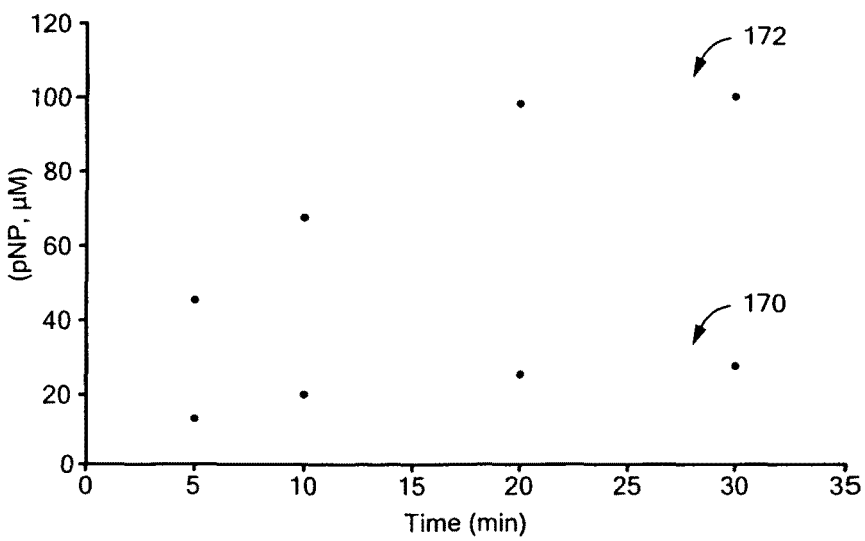
FIG. 14 depicts graphs showing the enhanced catalytic activity of the enzymes of the enzyme coating configured as an OPH coated cotton thread as a result of the refolding process in accordance with one or more embodiments of this invention.

Using a carefully controlled and adequate amount of β-cyclodextrin imbedded in the cross-linked matrix by changing the amounts of reactive hexyl isocyanates (HDI) (equivalences of β-cyclodextrin vs. hexyl diisocyanate), the amount of enzyme loading of the enzyme layer could also be maximized accordingly. The uptake of both chemical species (p-nitrophenol and methyl parathion) by the enzyme layer 46 of system 40, FIG. 4, and system 80, FIG. 7, was determined to demonstrate preferential sorption trends. In accordance with the systems and methods of one or more embodiments of this invention, absorptive but non-hyper-absorptive polymer containing Polyurethane-β-cyclodextrin (PU-β-CD)s were prepared as a physical support for enzymes, while absorptive towards toxins appropriate for safe disposal. PU-β-CDs are capable of forcing chemical species into their hydrophobic cavities by host-guest complex formation. As anticipated, experiments showed Polyurethane-β-CD coated with OPH enzyme showed a high sorption capacity for methyl parathion (MPT) and its breakdown product p-nitrophenol (p-NP). Graph 140, FIG. 12, shows one example of p-NP and MPT absorptive behavior of cotton thread coated with polyurethane layer 46, FIG. 4, including β-cyclodextrin as a function of hexyl diisocynate ratio.

II-1-2: Reactive Polyurethane-β-Cyclodextrin (R-PU-β-CD) as Decontaminating Synzyme The PU-β-CD produced in accordance with one or more embodiments of this invention shows an unexpected ability to absorb and hydrolyze MPT within 14 h, even in the absence of any enzyme catalyst.

In one example, samples from differently prepared Poly-β-CD were exposed to MPT for six days, the PU-β-CD material of one or more embodiments of this invention, and a control of stock MPT. Only the samples containing Poly-β-CD materials the material sorption reinforced catalytic system for the degradation of threat agents of this invention developed a characteristic yellow color of p-nitrophenol (pNP) as a result of degradation, albeit over a much longer time frame (e.g., 6 days) than that in the presence of enzyme (e.g., a few minutes). The catalytic activity became evident only after exposing β-CD in a cross-linked polymeric backbone, in absence of enzyme. In addition to their reactive capability, when coated with OPH and then exposed to MPT vapor in the presence of water vapor (100 μg), QNA cotton cloth functionalized with β-CD turned yellow over 8 h at 40° C. (Not shown here), indicative of the qualitative breakdown of MPT.

II-2: Hygroscopic D-(+)-Trehalose and its Highly Absorptive Polymeric Derivatives D-(+)-trehalose is known to stabilize enzymes at low temperatures and was also confirmed to stabilize enzymes during the immobilization process. In one example, polyurethane-D-(+)-trehalose (PTH) was prepared in a specific molar ratio optimized for catalytic sequestration of chemical warfare agents. This was prepared via coupling of D-(+)-trehalose with HDI in DMF at 70° C. for 8 hours. The product was then freeze-dried over several days and the resulting powder was sieved. Characterization was carried out by FT-IR (the $CO_2$ group was observed at 1725 $cm^{-1}$). The use of different amounts and types of alkyl spacers were employed to control the amount of trehalose incorporated in the polymer matrix, which subsequently affect the sorption capabilities and catalytic ability when enzymes were incorporated, along with hydrolytic capability against MPT.

These environmentally-benign, polymeric trehalose (PU-TH) molecules were demonstrated to have high binding efficiency for the enzyme catalyst, while maintaining their chemical activity to efficiently hydrolyze organophosphates, and the ability to act as sorption-induced hydrolyzing vehicles against chemical threat agents.

II-3: Calix[8]Arene and its Polymeric Derivatives for Sequestration of Radiological Waste Polyurethane-calix[8]arene (PU-CX) was prepared, in a similar preparation protocol of PU-β-CD, via coupling of calixarene with HDI in DMF at 70° C. for 14 hours. The OPH coated PU-CX particles were prepared and demonstrated to degrade MPT to pNP within about 5 minutes, as shown by graphs 162 and 164, FIG. 13. The particles of PU-CX could be potentially usable for sequestration of radiological waste.

II-4: Synthesis of Co-Pre-Polymers: Co-Polymeric Polyurethane-β-Cyclodextrin (PU-β-CD)/Poly-Urethane-D-(+)-Trehalose (PU-TH)/Polyurethane-Calix[8]Arene (PU-CX)

The enzyme based catalytic systems and methods of one or more embodiments of this invention appear to be promising when coupled with absorbing polymeric substrates (polyurethane-β-cyclodextrin (PU-β-CD), poly-calixarene (PU-CX) and polyurethane-D-trehalose (PTH)). In-situ chemical modification and incorporating of highly absorbing but regenerative molecular unit such as co-polymeric polyurethane of β-cyclodextrin, calixarene, and polymeric D-(+)-trehalose were conceived and demonstrated.

Environmentally-benign, light-weight polymeric pore-forming substrates were prepared as a physical support to safely harbor enzymes. β-cyclodextrin and its derivatives are known to sequester CWAs and TICs, such as Soman (GD) and also to capture into their cavities biological species through inclusion complex formation with their hydrophobic pocket. Thus, incorporation of β-cyclodextrin into porous polymers might impart excellent sorption capacities and additionally could achieve clean "air" chemistry by (1) decontamination followed by (2) sequestration, when biological catalysts are incorporated into the polymers. Its preferential sorption of MPT over pNP were also known. D-(+)-trehalose was demonstrated to protect enzymes and its hydrolytic and hygroscopic properties bring in moisture to the local environment.

Reaction of β-cyclodextrin, calixarene, and polymeric D-(+)-trehalose in a specific ratio with HDI produced insoluble absorptive particles via coupling of β-cyclodextrin, D-(+)-trehalose and/or calixarene with HDI in DMF at 70° C. for 14 hours. These co-polymeric particles were demonstrated to be chemically inert and robust enough to endure extended exposure to highly acidic and highly alkaline media.

Part III Immobilization of DECON Enzymes to Absorptive Polymer Substrates

III-1. Stabilization of Enzymes with β-CD-BPEI and its Oligomeric Derivatives

The long term operational stability of any enzyme system is critical because enzymes aggregate easily upon exposure to stressful conditions. Due to their amphoteric nature enzymes naturally degrade over time, but within the matrix the enzymes degrade more slowly even after cycled use over time under stressful conditions. In enzyme folding situations, chaperone molecules are known to assist them in reaching a specific conformation through different mechanisms.

OPH and a number of other enzyme systems have been shown to regain lost activity under certain conditions. These include the use of a specific buffered solution and the inclusion of "chaperone" molecules in enzyme formulations. The OPH-PU-β-CD cotton threads of the systems and methods of one or more embodiments of this invention were demonstrated to have much greater activity after they were refolded in 2-(N-Cyclohexylamino)ethane Sulfonic Acid (CHES) buffer solution and β-cyclodextrin as a chaperone at low temperature (7° C.).

In one example, β-CD-BPEI cotton thread, e.g., about 1 m long, was washed carefully with DMF followed by MeOH in a 50 mL size glass beaker. It was coated with OPH enzyme and used to degrade fresh MPT solution. The results were recorded, as shown by degrading kinetics curve 170, FIG. 14, (20 μM pNP after 30 min). After use, the OPH thread was washed using CHES buffer briefly to eliminate MPT drops left on the thread. A few drops of CHES buffer were added to the coated cotton thread, and then placed in a freezer (7° C.). After 48 h, the thread was withdrawn from the freezer and exposed to a fresh 10 mL MPT solution to monitor the subsequent catalytic degradation of "used" OPH thread. Curve 172 shows the results of the catalytic activity as a result of the refolding process.

This experimental result of enhanced activity using an artificial chaperone was also reproduced on OPH-nylon substrates (Biodyne B-membrane, Pall Corporation) when coated with OPH enzyme by known procedure. It was determined that once enzymes are anchored an artificial chaperone could serve to refold the enzymes incorporated within the catalytic multilayer system. Both BPEI and CD-BPEI stabilized OPH enzyme survived stressful conditions (e.g., rain, light, and heat), when coated by a certain protocol, meaning that BPEI and CD-BPEI serve as a chaperone to the OPH.

III-2. Stabilization of Enzymes with D-(+)-Trehalose and its Oligomeric Derivatives D-(+)-trehalose and its derivatives were tested as a chaperone to repair denatured OPH enzyme. D-(+)-trehalose, a dimeric glucopyranose, protects and stabilizes the structure and activity of a variety of enzymes at low temperatures, and helps them to refold when denatured. Trehalose was reported to display chaperone-like activity by stabilizing the native conformation of enzymes and protecting them from various kinds of stresses. Along with β-CD and its derivatives, trehalose could stabilize the enzyme within the matrix at ambient conditions and particularly at low temperatures. The trehalose was employed during the drying of the OPH enzyme at low temperature and it also helped to stabilize it during the immobilization process, when cross-linked with vaporous glutaraldehyde and its derivatives.

III-3 Fixation of Enzymes by Polyimine Formation Using Vaporous Glutar Di-Aldehyde (GA) and its Derivatives As was discussed above, the mode of enzymes immobilization is not layer-by-layered assembly but a physical adsorption in presence of enzyme-stabilizing D-(+)-trehalose, preferably followed by controlled vapor phase cross-linking via glutaraldehyde and its derivatives. The specific and selective cross-linking occurs preferably with secondary amine groups to form imine bridges, as well as with some primary amines. In that manner, the "active" enzyme content could be increased in a controlled manner. Layering of individual coated fabrics is another approach for getting higher capacity for chemical absorption and catalytic activity. Methods of attaching the particles and coatings have an impact on the reactivity of the system.

VI. End Capping Polymeric BPEI Having β-Cyclodextrins and Derivatives as Mesogens. VI-1. β-CD-BPEI and its Polymeric and Oligomeric Derivatives of Ethylenimine (OEI)

Figure 15:
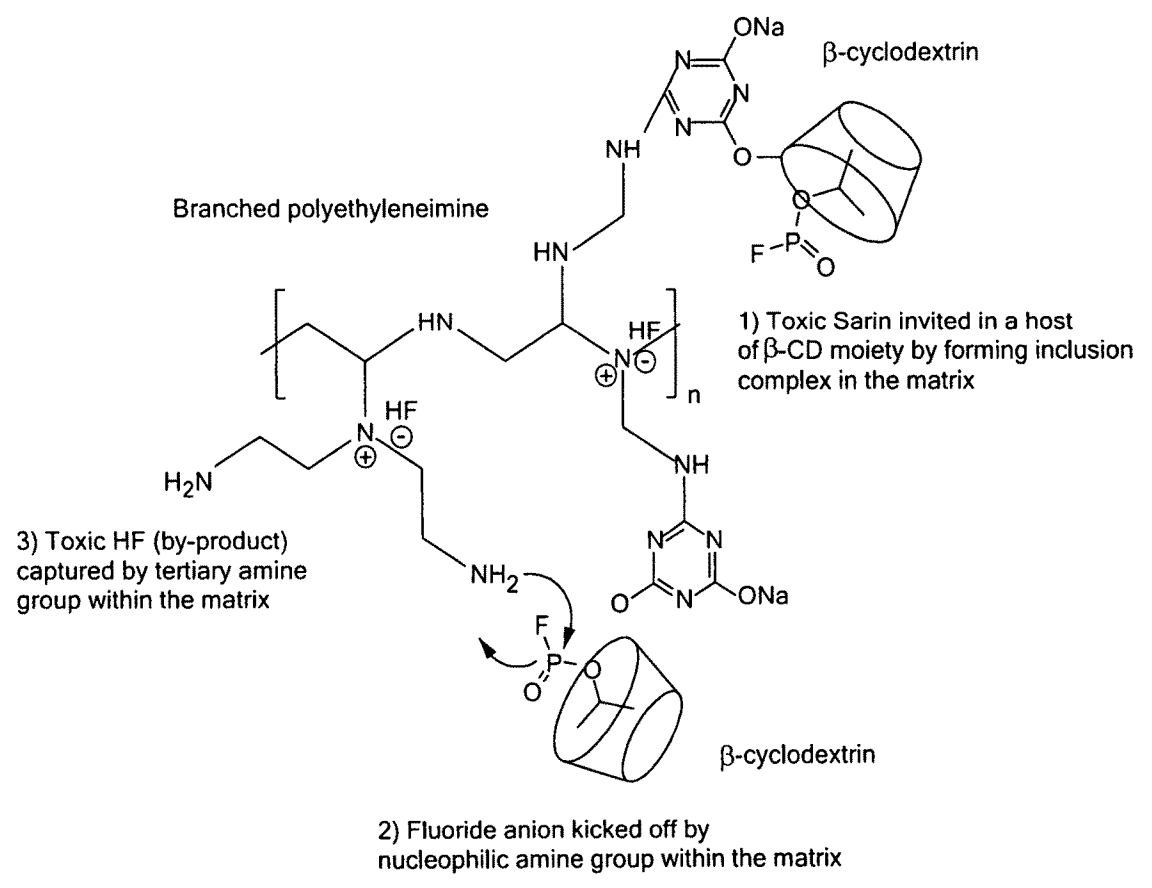

Polyethyleneimine (PEI) is known to possess enzyme-like catalytic behavior in organic reactions to breakdown phenyl esters at a high turnover rate. This may be employed as another method to bring on catalysts in accordance with one or more embodiments of this invention. While the turnover rate for BPEI is lower than enzymes, BPEI's resilience to stressful environments makes it a prime co-reactant in providing comprehensive aerosol protection in all environments. This activity was further increased through the formation of β-CD-BPEI which allows for an even quicker reaction rate when compared to standard BPEI. FIG. 15 depicts the hypothetical catalytic processes of β-CD-BPEI for the decontamination of the sarin (GB) toxin.

Branched PEI (BPEI) with alkyl groups, e.g., a propyl group or similar type group, are capable of forming a compact conformation to resist water at the interfacial area and better served as nucleophilic chemical moieties than those of linear PEI (LPEI). One key element may be to make the lone pair electrons of nitrogen group available in such polyethylenimine derivatives. Steric bulkiness of branched PEI may cause less substituted β-CD units, thus resulting in co-exiting of nucleophilic primary (1°) amine, highly basic tertiary (3°) amine, while allowing for an adequate amount of β-CD for hosting incoming toxins into its interior. β-CD-BPEI may serve as a chaperone for OPH enzyme, a potential reactant for blood gases and toxic industrial materials, a neutralization reagent for acid gases, and may cause slow hydrolytic degradation of chemical nerve agents upon encounter. For example, when toxic sarin (GB) comes in contact with the system of one or more embodiments of the invention, the GB will make a complex of inclusion into β-cyclodextrin moiety, which maximizes residence time near reactive component prior to attack of primary amine group at the fluorophosphonyl group. The leaving fluoride anion thus could be removed by the nucleophilic amine group within the BPEI matrix. Also toxic "Hydrofluoric acid" (HF) breakdown product can be captured by highly "basic" tertiary amine group within the matrix for comprehensive and complete decontamination.

Figure 16:
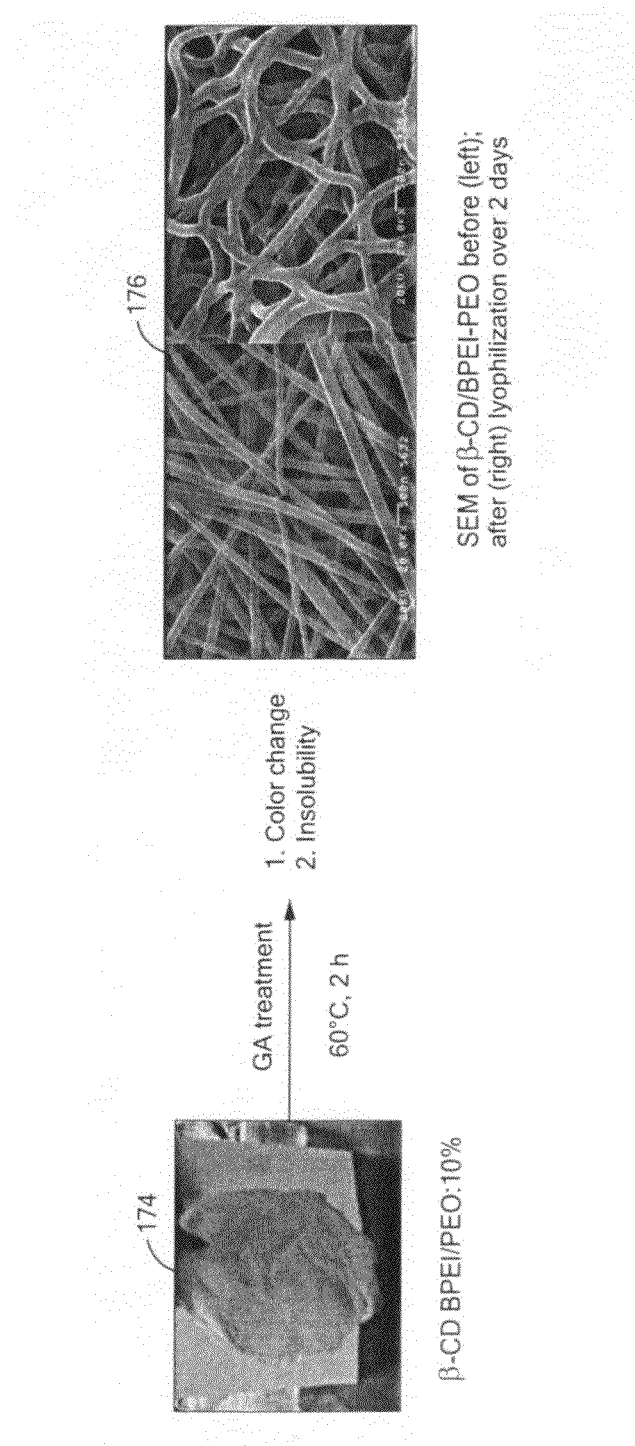
FIG. 16 are photographs depicting electrospun nanofiber mats before and after lyophilization in accordance with one embodiment of this invention.

In one example, the β-CD-BPEI was prepared in aqueous medium at 70° C. from a reaction of branched polyethyleneimine (BPEI) with monochlorotriazinyl-β-cyclodextrin (MCT-β-CD). In this example, the β-CD-BPEI was prepared as electrospun nanofiber mats 174, FIG. 16, co-spun with poly(ethylene oxide) in a 1 to 1 ratio. Lyophilization of the mat allowed much of the open structure to be maintained, e.g., 200 nm fiber diameter, as shown at 176.

In order to create these absorptive and reactive materials, branched polyethyleneimine (BPEI), e.g., having a molecular weight of about 70,000, 20,000, 7,000,600 Daltons, and the like, was treated in a reaction vessel with monochlorotriazinyl β-cyclodextrin (MCT-β-CD) in alkaline aqueous solution (pH 8.0) at 90° C. for 18 h to produce β-CD bonded polyethylenimines derivatives. After the reaction, the resulting solution turned a mild yellow to a yellowish-green color, depending on the amount of β-CD bonded to the backbone of polymers. According to two UV-VIS absorption spectra put in the same frame, the absorption band was shifted from 230 nm to 374 nm. This indicates that attachment of UV-active (but colorless by appearance) chlorotriazinyl β-CD to the backbone of branched polyethylenimine progressed over time. The degree of attachment and the processability of the polymeric powders (yellow green) may be determined using standard protocol.

VI-2. Fixation of Reactive BPEI Using Vaporous Glutaraldehyde (GA) in Gas Phase

Figure 17:
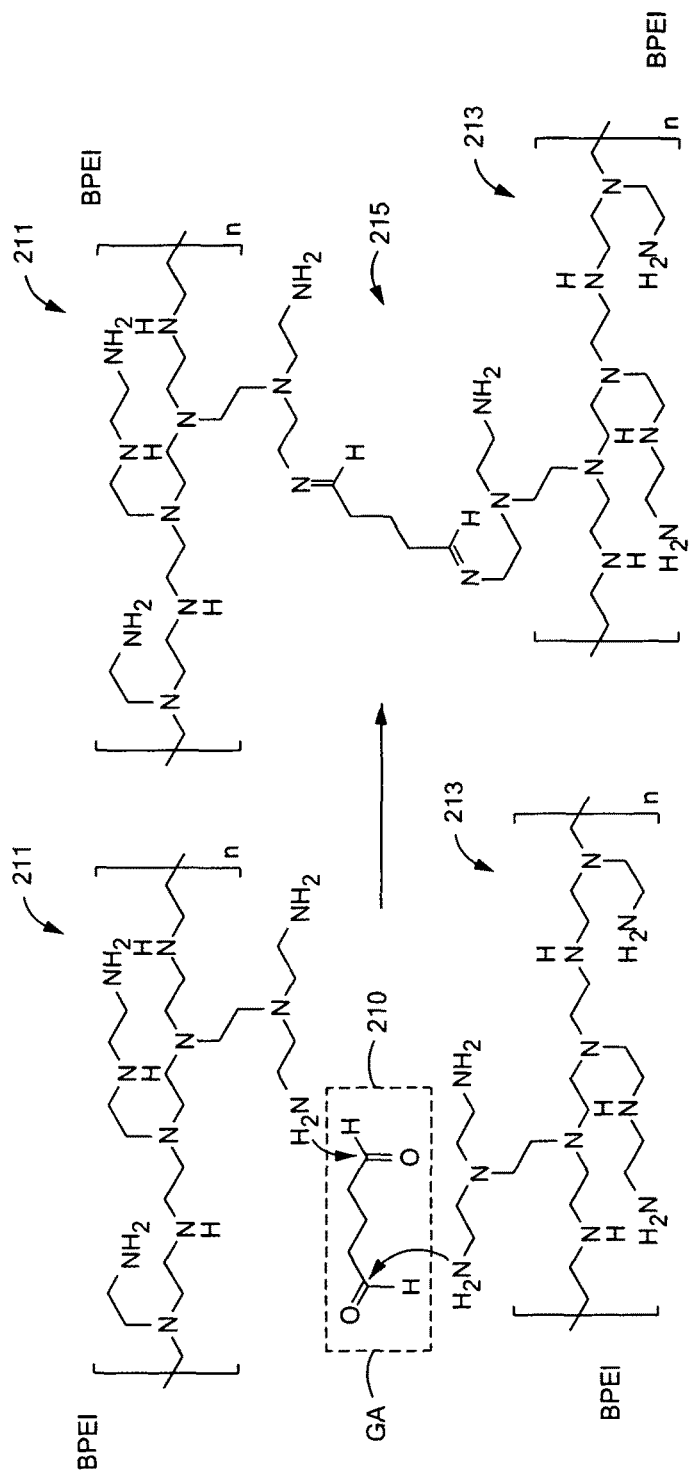
FIG. 17 depicts the binding of two BPEI molecules using a GA as a binding agent.

Imine formation using glutaraldehyde (GA) is commonly employed in organic and/or biochemistry. For example, GA-210, FIG. 17, preferably reacts first with secondary amines then primary amines to bind BPEI molecules 211 and 213 together, as shown. The reacted GA-210 is shown at 215. This has been demonstrated by mixing low level solutions of GA and BPEI together, and seeing the formation of particulates.

This complex formation is highly random and typically cannot be controlled in water or organic solvent. However, it may be controlled by diluting the amount of GA present in vapor phase for a brief exposure at ambient conditions. To selectively attach enzymes into absorptive polymers while avoiding multipoint attachment of enzymes, and to anchor β-CD-BPEI subsequently to the enzymes layers in accordance with one or more embodiments of this invention, a controlled attachment in gas phase at ambient conditions was conceived and demonstrated. BPEI, as a base and an acid scavenger, remains nucleophilic after GA treatment in gas phase at ambient conditions. Schiff Base formation between BPEI and GA is minimized in the vapor phase exposure as compared to reactions in solution.

The optimization of gaseous GA binding agent was performed to optimize both reactivity and retention of substrates to the fabric. For this a simple fume-chamber was utilized at room temperature in which liquid GA was allowed to vaporize and generate fumes. A set of samples was placed into the chamber and allowed to react for a set of pre-determined times. After the samples were taken out and dried their activity against MPT was tested. FIG. 18 shows graphs 180 and 182 which represent the data collected. The samples were left in the chamber from 30-720 minutes to get a good spread. Both sets of data, indicated by graphs 180 and 182, show that 2 hour (120 min) exposure of the fabric to GA fumes provides the best activity while still maintaining flexibility and robustness of the fabric itself.

Through the utilization of gas phase coupling of secondary amines between enzymes via glutaraldehyde (GA) to form inime bridges, the active site is maintained allowing for the preservation of its chemical activity throughout the coating protocol, while at the same time anchoring it to the substrate. At the same time, nucleophilic primary amine groups remain intact as created in-situ in the capping layer of CD-BPEI and its derivatives.

Testing of the System.

The sorption reinforced catalytic system for the degradation of threat agents of one or more embodiments of this invention may be based on embedding a sorption-reinforced decontaminating layer of biocatalytic nanoparticles into the desired high-surface-area meltblown fabrics in order to be able to decontaminate all classes of chemical agents while at the same time allowing for safe disposal of the agents' reaction products via host-guest-complex formation. Active decontaminating enzymes against G, V and H CWA agents may include organophosphorous hydrolase (OPH), organophosphorous acid anhydrolase (OPAA) and haloalkane dehalogenase (HD). These enzymes were sequentially incorporated into highly absorbing polymeric substrates/particles and ultimately onto fabrics to create a comprehensive catalytic system. The catalytic actions were performed through the use of highly absorbing polymeric substrates to absorb CWA and TIC simulants and release their byproducts for safe disposal and subsequent recycled use. These enzyme-friendly self-decontaminating systems are an efficient platform for destroying biological and chemical threat agents.

Status of Performance Testing

The sorption reinforced catalytic coating system and method for the degradation of threat agents of one or more embodiments of this invention may be capable of decontaminating chemical nerve agents at ambient conditions (temperature, moisture, and the like) in a closed environment, using a simplified flow-through air system in aqueous medium and direct agent exposure without solvent medium, followed by the sequestering of breakdown byproducts for safe disposal at a later time.

The sorption reinforced catalytic coating system and method for the degradation of threat agents may be incorporated onto cotton, cotton-nylon, modified nylon, meltblown and electrospun fiber-mats of PE/PA, PU, and similar type materials, as discussed in the following examples from third party testing facilities.

Figure 19:
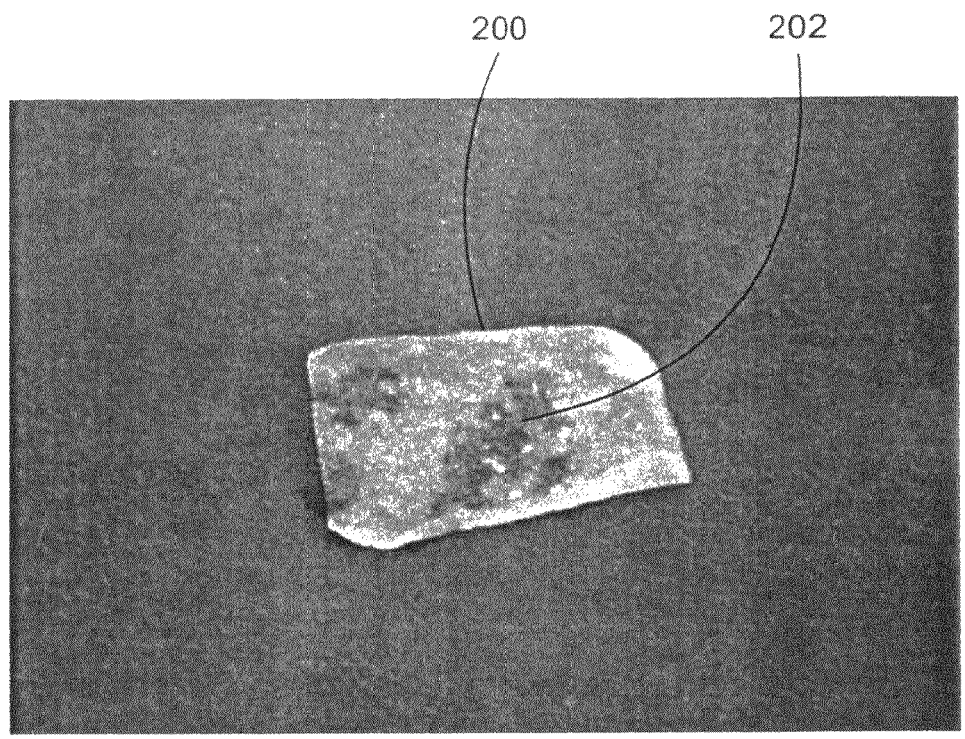
FIG. 19 is a photograph showing the enzyme coating of one or more embodiments of this invention coated on a fabric and being exposed to colorless toxin and showing the development of a distinctive color of the pNP degradation by-products.

In one example, degradation of nerve agent stimulant, e.g., more than about $10 \, g/m^2$, was achieved using system 80, FIG. 7 with material 44 configured as a meltblown (MB) fabric within a couple of hours of exposure in aqueous medium. The treated MB fabrics 200, FIG. 19 of system 80, FIG. 7, turned yellow, indicated at 202, FIG. 19, as a result of decontamination. This indicates system 80 on the MB fabric absorbed the breakdown product of the decontamination reaction (p-nitrophenol). This was reproduced using the same MB fabric during multiple runs. The same MB fabric also effectively degraded Soman (GD) as shown by graphs 204, FIG. 20. In this example, measured concentration of the degradation products was fluoride.

Self-Decontaminating OPH-MB Nanofiber Mats

Figure 21:
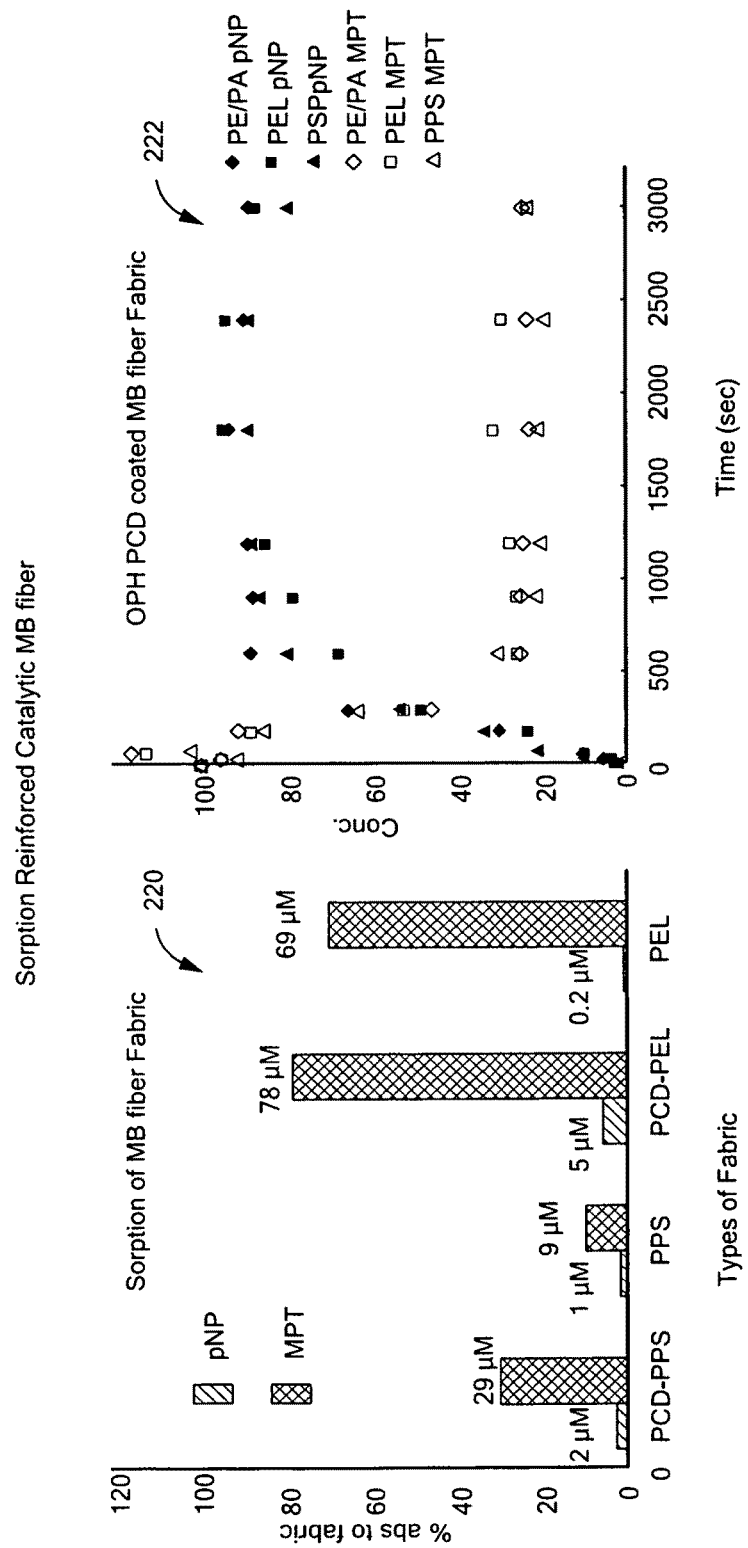
FIG. 21 depicts graphs showing the sorption and decontaminating capacity of OPH coated Poly-β-CD MB fibers in accordance with one or more embodiments of this invention.

In one example, OPH enzyme was coated onto MB nanofibrous substrates employing the coating system of one or more embodiments of this invention. The retention of the catalytic activity of the enzyme on the fibrous substrates were confirmed and reproduced by showing immediate decontamination of the CWA simulant. See graphs 220 and 222, FIG. 21.

Figure 22:
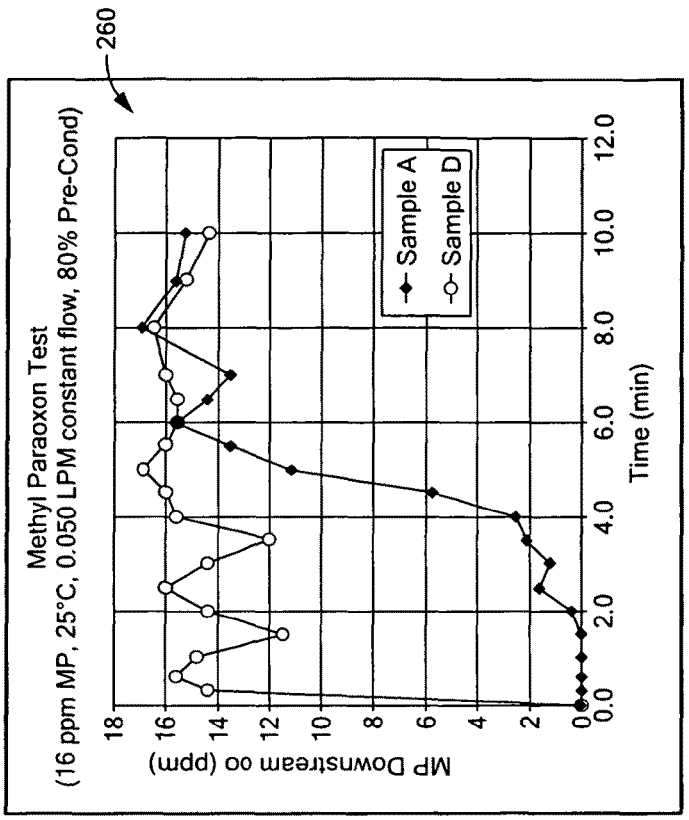
FIG. 22 shows graphs depicting testing of one embodiment of the sorption reinforced catalytic coating system for the degradation of threat agents of one embodiment of this invention which was tested by a third party.

Testing by a third party, Assay Tech, Inc., Boardman, Ohio was performed on system 80, FIG. 7, deposited onto a fiber mat. These samples were challenged with a constant concentration of CWA simulant MPO. The sample showed a capacity to sequester completely the challenge material for a short time before a visible break though occurred. The recorded break though time is relatively short for these samples due to the high porosity of the fabric used. See graphs 260, FIG. 22.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. A coating system for the degradation of threat agents comprising:
    a synzyme coating about a material configured to degrade the threat agents, the synzyme coating including sorption molecules configured to sorb the threat agents; and
    a binding agent configured to selectively attach the synzyme coating to the material to maximize loading and retention of the synzyme coating on the material.

2. The system of claim 1 in which said sorption molecules are configured to increase residence time of the threat agents in the synzyme coating.

3. The system of claim 2 in which said sorption molecules include cyclodextrin and derivatives thereof.

4. The system of claim 2 in which the cyclodextrin and derivatives thereof include β-cyclodextrin, γ-cyclodextrin, and α-cyclodextrin.

5. The system of claim 1 in which the synzyme coating includes polyimine.

6. The system of claim 5 in which the polyimine is branched.

7. The system of claim 6 in which the branched polyimine includes branched polyethylenimine (BPEI).

8. The system of claim 7 in which the branched polyethylenimine is functionalized with cyclodextrin and derivatives thereof.

9. The system of claim 8 in which the branched polyethylenine includes amines which degrade the threat agents.

10. The system of claim 9 in which the amines include primary amines.

11. The system of claim 1 in which the sorption molecules include an inner hydrophobic pocket for attracting and increasing the residence time of the threat agents and for expelling hydrolytic degradation products of the threat agents.

12. The system of claim 1 in which the binding agent includes aldehyde functionalized binders.

13. The system of claim 12 in which the binding agent includes glutaraldehyde (GA).

14. The system of claim 13 in which the glutaraldehyde is vaporized.

15. The system of claim 13 in which the glutaraldehyde is configured to selectively attach to the synzyme coating.

16. The system of claim 15 in which the glutaraldehyde selectively attaches to free amines of a branched polyethylenimine.

17. The system of claim 16 in which the free amines include secondary amines.

18. The system of claim 15 in which the glutaraldehyde is configured to attach to the synzyme layer to prevent delamination.

19. The system of claim 15 in which the glutaraldehyde is configured to attach to the synzyme coating to render the synzyme coating insoluble in water.

20. The system of claim 1 in which the binding agent is configured to provide for repeated cleaning cycles of the coating system.

21. The system of claim 1 in which the binding agent is configured to provide for reusability of the coating system.

22. The system of claim 1 in which the synzyme coating is configured to degrade the threat agents in a low moisture environment.

23. The system of claim 1 in which the threat agents include toxic industrial chemicals.

24. The system of claim 1 in which the threat agents include chemical warfare agents.

25. The system of claim 1 in which the material includes fiber-based fabrics.

26. The system of claim 1 in which material includes melt-blown nano based fabrics.

27. The system of claim 1 in which the material includes electrospun nano fibers.

28. The system of claim 1 in which the material includes cotton.

29. The system of claim 1 in which the material includes nylon.

30. A method for making a coating system for the degradation of threat agents, the method comprising:
　　coating a material with a synzyme coating configured to degrade the threat agents, the synzyme coating including sorption molecules configured to sorb the threat agents; and
　　exposing the synzyme coating to a binding agent configured to selectively attach the synzyme coating to the material to maximize loading and retention of the synzyme coating on the material.

* * * * *